United States Patent
Quintero et al.

(10) Patent No.: US 10,219,793 B2
(45) Date of Patent: Mar. 5, 2019

(54) DELIVERY SYSTEMS FOR FLOWABLE SUBSTANCES STORED IN SQUEEZABLE CONTAINERS

(71) Applicant: Ethicon, Inc., Somerville, NJ (US)

(72) Inventors: Julian Quintero, Flemington, NJ (US); Jianxin Guo, Livingston, NJ (US); Keith A. Pinto, Hoschton, GA (US)

(73) Assignee: Ethicon, Inc., Somerville, NJ (US)

( * ) Notice: Subject to any disclaimer, the term of this patent is extended or adjusted under 35 U.S.C. 154(b) by 0 days.

(21) Appl. No.: 15/669,015

(22) Filed: Aug. 4, 2017

(65) Prior Publication Data

US 2019/0038271 A1 Feb. 7, 2019

(51) Int. Cl.
*A61B 17/00* (2006.01)
*B65D 47/36* (2006.01)
*B65D 83/00* (2006.01)

(52) U.S. Cl.
CPC ........ *A61B 17/00491* (2013.01); *B65D 47/36* (2013.01); *B65D 83/0055* (2013.01)

(58) Field of Classification Search
CPC .............. A61B 17/00491; B65D 47/36; B45D 83/0055; B05C 17/005
USPC ........................................... 222/93, 105–107
See application file for complete search history.

(56) References Cited

U.S. PATENT DOCUMENTS

| 4,732,147 A | 3/1988 | Fuller | |
| 4,899,748 A | 2/1990 | Gross | |
| 5,042,690 A * | 8/1991 | O'Meara | A45D 34/042 206/15.2 |
| D345,796 S | 4/1994 | Pernicka | |
| D379,655 S | 6/1997 | Savignac | |
| 5,678,731 A * | 10/1997 | Okamura | B65D 35/28 222/105 |
| 5,711,453 A * | 1/1998 | Weiler | B65D 47/14 222/541.2 |
| D439,976 S | 4/2001 | Cote | |
| D449,685 S | 10/2001 | Morrison | |
| D450,676 S | 11/2001 | Huttner | |

(Continued)

FOREIGN PATENT DOCUMENTS

| DE | 102012004510 | 9/2013 |
| EP | 521200 | 4/1996 |

(Continued)

*Primary Examiner* — Lien Ngo
(74) *Attorney, Agent, or Firm* — Doherty IP Law Group LLC

(57) ABSTRACT

A delivery system for flowable substances includes a squeezable container having a sealed proximal end, a sealed distal end having a dispensing neck, and an outer wall that surrounds a storage reservoir. The delivery system has a container support frame assembled with the squeezable container having a proximal edge secured to the sealed proximal end of the squeezable container, a distal edge secured to the dispensing neck of the squeezable container, and first and second lateral edges extending between the proximal and distal edges and overlying opposing sides of the squeezable container. The proximal and distal edges and the first and second lateral edges define a central opening of the container support frame that provides access to the outer wall of the squeezable container. The container support frame has an elongated handle that extends proximally from the proximal edge of the container support frame.

17 Claims, 13 Drawing Sheets

(56) References Cited

U.S. PATENT DOCUMENTS

| | | | |
|---|---|---|---|
| 6,315,165 B1 | 11/2001 | Regan | |
| 6,770,076 B2 | 8/2004 | Foerster | |
| D496,460 S | 9/2004 | Glaesel | |
| 6,968,978 B1 | 11/2005 | Matthews | |
| 7,918,621 B2 | 4/2011 | Battisti | |
| 8,056,748 B2 * | 11/2011 | Chen | B65D 50/041 |
| | | | 215/334 |
| 8,287,202 B2 | 10/2012 | Goodman et al. | |
| 8,807,859 B2 | 8/2014 | Stenton | |
| D785,793 S | 5/2017 | Landanger | |
| D786,428 S | 5/2017 | Peltosaari | |
| D792,587 S | 7/2017 | Owens et al. | |
| D792,968 S | 7/2017 | Galitz et al. | |

FOREIGN PATENT DOCUMENTS

| | | |
|---|---|---|
| WO | 2012164779 | 6/2012 |
| WO | 2014083570 | 6/2014 |

* cited by examiner

DELIVERY SYSTEMS FOR FLOWABLE SUBSTANCES STORED IN SQUEEZABLE CONTAINERS

BACKGROUND OF THE INVENTION

Field of the Invention

The present patent application is generally related to medical devices, and is more specifically related to delivery systems used to dispense flowable substances from squeezable containers.

Description of the Related Art

There are many different ways to close wounds that result from surgical incisions and accidental lacerations including using sutures, using surgical staples, using surgical skin tapes, and using adhesive compositions that are applied to skin.

Sutures are generally recognized as providing adequate wound support for the duration of wound healing, however, suturing involves additional trauma to the wound because the needle and suture material must pass through the tissue at the margins of the wound. Suturing can also cause cosmetically unattractive wound closure marks and can be time consuming. In addition, depending on techniques and the types of sutures used, sutures may need to be removed at a later date, which could require further medical attention and cause more pain and trauma to a patient In terms of cosmetic results, surgical staples have many disadvantages that are similar to those described above for sutures. Removing staples can be painful and, depending on the location and the patient's pain threshold, may require the use of topical anesthesia. Recently, absorbable staples have been developed that are absorbed by the patient's body over time and do not have to be removed.

Skin closure strips, such as conventional adhesive bandages, are typically utilized for closing relatively superficial skin wounds, however, their use is limited to only certain types and degrees of wounds. The contact adhesives that are used with skin closure strips typically retain holding power for no more than a day or two and can lose holding power quickly in the presence of moisture (e.g., perspiration).

The direct application of adhesives to tissue and skin has also been used for wound closure purposes. For example, monomer and polymer adhesives are used in medical applications. Since the discovery of the adhesive properties of such monomers and polymers, they have found wide use in medical applications due to the speed with which they cure, the strength of the resulting bond formed, and their relative ease of use. One widely used topical skin adhesive product is sold under the trademark DERMABOND® by Johnson & Johnson Corporation of New Brunswick, N.J.

Adhesives, pastes and thixotropic substances used for medical procedures are typically stored in deformable containers or tubes. Deformable tubes are usually made of metals or plastics that are squeezable for dispensing the adhesive. Squeezing a metal or plastic tube by hand expresses the substance contained in the tube through a delivery nozzle. This can be a tricky and messy operation especially when the tube is not completely full. Moreover, the amount of substance being expressed is not easy to regulate by pressing with fingers, and it is difficult to simultaneously regulate the amount that is dispensed while the adhesive is being applied to a substrate.

In order to overcome the above-identified problems, there have been many activities directed to developing delivery devices for dispensing flowable substances. For example, U.S. Pat. No. 6,315,165 to Regan discloses a device for expressing substances from a deformable tube. The device includes a casing with side wall apertures and two opposing jaws that pass through the respective apertures for gripping and expressing a flowable substance from the tube.

EP521200B1, assigned to Loctite Ltd., discloses a device for the controlled delivery of liquid and/or pasty substances contained in a yieldable tube. The device has a gripper element provided with jaws for receiving the tube between them, a casing containing the gripper element, the jaws which are accessible through apertures provided in opposing walls of the casing, and a delivery nozzle for the tube that extends through an axial opening in the casing.

U.S. Pat. No. 8,807,859 to Stenton discloses a liquid applicator device having a hollow body with a reservoir that contains a liquid. The device has an actuator that moves a plug for squeezing the walls of the reservoir to discharge the liquid from the reservoir via an outlet. The liquid is retained in the reservoir, which is sealed by the plug until usage.

U.S. Pat. No. 5,042,690 to O'Meara discloses a dispensing device including a tube with a nozzle mounted on one end of the tube and having a thin wall seal that is punctured to provide a discharge at the other end of the nozzle. The dispensing device has a cap with a first end having an inside cross section sized to engage the nozzle and having an axially centered puncture spike movable to a position to puncture the thin wall seal. The puncture spike has a chisel shaped edge for forming a hole in the thin wall seal and a central bore for providing access to the contents of the tube.

In spite of the above advances, there remain many problems associated with conventional delivery systems and devices for flowable substances. First, leakage of the flowable substance can result when a dispensing cap is closed at the same time that piercing of a seal is performed. Second, a collapsible container or tube may deform and partially collapse during the closing and piercing operations, which may result in undesirable, accidental leakage of the adhesive. There also remains a need for delivery systems and devices that separate and/or isolate the step of piercing a seal from the step of dispensing a flowable substance from a container, that provide protection to the container, that improve ergonomics, and that facilitate accurate placement of the dispensed flowable substance (e.g., an adhesive).

SUMMARY OF THE INVENTION

The present patent application is related to delivery systems for expressing flowable substances from squeezable containers such as a deformable tube. In one embodiment, the squeezable containers may be yieldable tubes made of metal, plastic, and/or cellulose. Examples of deformable containers may include those containing pasty or thixotropic substances such as adhesive In one embodiment, a delivery system for storing and dispensing a flowable substance such as a polymerizable adhesive preferably includes a squeezable container, such as a collapsible or compressible tube closed at a proximal end by folding the tube and having a dispensing neck with a male threaded portion at a distal end. In one embodiment, the distal end of the squeezable container is desirably sealed by a frangible or pierceable seal, such as a frangible foil.

In one embodiment, a delivery system preferably includes a hollow cylindrical connector having female treads on a proximal end thereof that match the male threads at the distal end of the squeezable container. In one embodiment, a plurality of turns of the connector are required to fully attach and seal the connection between the connector and the squeezable container. In one embodiment, the connector preferably has a male luer connection and a male threaded portion of a distal end thereof. In one embodiment, the connector desirably has an internal cylindrical channel for passing an adhesive or liquid through the connector.

In one embodiment, the delivery system preferably includes a piercer, such as a hollow cylindrical piercer, adapted to slide inside the connector. In one embodiment, the piercer desirably has an internal cylindrical channel for passing a liquid or an adhesive and a sharpened proximal end for breaking and/or piercing a seal.

In one embodiment, the delivery system preferably has a filter, such as a cylindrical porous filter, impregnated with a chemical initiator, activator, catalyst, crosslinker, and/or other additives that are disposed within the filter and/or the connector. In one embodiment, the filter may be impregnated with an accelerator of polymerization. In one embodiment, the filter is configured to slide inside the connector between proximal and distal ends of the connector. In one embodiment, the piercer and the filter are disposed inside the cylindrical channel of the connector with the filter being distal to the piercer. In one embodiment, the filter and the piercer are disposed within the male luer fixture of the connector.

In one embodiment, the delivery system preferably includes a dispensing cap, such as a cylindrical dispensing cap having a female threaded portion at a proximal end thereof that is configured to mate with male threads provided on an outer surface of a male luer fixture at the distal end of the connector. In one embodiment, the dispensing cap preferably has a dispensing aperture provided at a distal end thereof. In one embodiment, the dispensing cap desirably has a female luer fixture that matches the male luer fixture on the connector. In one embodiment, the dispensing cap and the threads are configured so that less than one full turn of the dispensing cap is required to advance the piercer proximally to pierce a frangible seal and to seal the luer connection between the distal end of the connector and the proximal end of the dispensing cap.

In one embodiment, the delivery system preferably includes a container support frame that is shaped and configured to surround and immobilize the squeezable container. In one embodiment, the container support frame preferably leaves major portions of the squeezable container uncovered and engages the squeezable container substantially at the periphery of the container. In one embodiment, the delivery system desirably includes an elongated handle secured to a proximal end of the container support frame and extending proximally from a proximal edge of the container support frame. In one embodiment, the elongated handle may be detachable from the container support frame. In one embodiment, the elongated handle desirably ensures enhanced control over the squeezable container and provides for ease of use and accuracy of delivery of the flowable substance and, therefore, improved cosmetics.

In one embodiment, the delivery system preferably eliminates leaking of liquids (e.g., adhesives) and provides for an ergonomic, controllable application of the liquid to a substrate.

In one embodiment, a delivery system for flowable substances such as skin adhesives applied to wounds preferably includes a squeezable container including a sealed proximal end, a distal end having a dispensing neck, and an outer wall extending between the sealed proximal end and the distal end that surrounds a storage reservoir of the squeezable container.

In one embodiment, a delivery system preferably includes a container support frame assembled with the squeezable container, the container support frame having a proximal edge that is secured to the sealed proximal end of the squeezable container, a distal edge that is secured to the dispensing neck of the squeezable container, and first and second lateral edges extending between the proximal and distal edges and overlying opposing sides of the squeezable container. In one embodiment, the proximal and distal edges and the first and second lateral edges define a central opening of the container support frame that defines a central opening that provides access to the outer wall of the squeezable container.

In one embodiment, the container support frame desirably includes an elongated handle that extends proximally from the proximal edge of the container support frame. In one embodiment, the elongated handle preferably includes an elongated blade having a proximal end with a rounded surface. In one embodiment, the elongated blade desirably has flat top and bottom surfaces that extend between the proximal edge and the rounded surface. In one embodiment, the flat top surface preferably includes markings for measuring distances such as the length of a wound.

In one embodiment, the squeezable container may be a compressible tube made of materials such as metals, plastics, and cellulose. In one embodiment, the storage reservoir of the squeezable container may contain a liquid polymerizable adhesive.

In one embodiment, the squeezable container has external threads provide on the dispensing neck. In one embodiment, the squeezable container desirably has a breakable or frangible seal located between a distal end of the dispensing neck and a distal end of the storage reservoir. The seal may be selectively broken for dispensing the flowable substance from the container.

In one embodiment, a delivery system for dispensing flowable substances preferably includes a connector having a proximal end with female threads that are threaded onto the external threads of the dispensing neck. In one embodiment, the connector desirably has a distal end with a male luer fitting having external threads and a connector flow channel located inside the male luer fitting.

In one embodiment, the delivery system may include a dispensing cap having a proximal end including a female luer fitting that matches the male luer fitting of the connector. In one embodiment, the dispensing cap preferably has female threads that mesh with the external threads of the male luer fitting of the connector. In one embodiment, the dispensing cap desirably includes a distal end with a dispensing aperture and a dispensing cap flow channel that extends proximally from the dispensing aperture.

In one embodiment, the delivery system desirably has a piercer disposed inside the dispensing cap and within the connector flow channel of the connector. In one embodiment, the piercer desirably has a proximal end with a sharpened surface or point for piercing the breakable seal. In one embodiment, the piercer is configured to slide inside the connector flow channel.

In one embodiment, the female threads of the dispensing cap are preferably rotatable about the external threads of the male luer fitting of the connector for moving the dispensing cap proximally, which, in turn, advances the piercer proximally for piercing the breakable seal with the sharpened surface of the piercer.

In one embodiment, the piercer may have a piercer flow channel that is in axial alignment with the connector flow channel and the dispensing cap flow channel.

In one embodiment, the dispensing cap preferably has a ring shaped groove that surrounds the dispensing cap flow channel and that is configured to seat a distal end of the male luer fitting of the connector.

In one embodiment, the delivery system preferably includes a porous filter impregnated with a chemical initiator, which is disposed within the connector flow channel between a distal end of the piercer and a proximal end of the dispensing cap flow channel. The filter may also include an activator, catalyst, crosslinker or other additives that are disposed within the connector or between the distal end of the container and the dispensing aperture of the dispensing cap. In one embodiment, the porous filter is preferably configured to slide inside the connector flow channel.

In one embodiment, the delivery system may have a dispensing cap having a proximal end with female threads that mesh with the external threads of the dispensing neck of the squeezable container. In one embodiment, the dispensing cap desirably includes a distal end with a dispensing aperture and a dispensing cap flow channel that extends proximally from the dispensing aperture. In one embodiment, a piercer is disposed inside the dispensing cap and is proximal to the dispensing cap flow channel. In one embodiment, the piercer preferably has a proximal end with a sharpened surface. In one embodiment, the dispensing cap is rotatable about the external threads of the dispensing neck of the squeezable container for moving the dispensing cap proximally, which, in turn, advances the piercer proximally for piercing the breakable seal with the sharpened surface of the piercer.

In one embodiment, a porous filter impregnated with a chemical initiator is disposed inside the dispenser cap between a proximal end of the dispensing cap flow channel and a distal end of the piercer.

In one embodiment, a delivery system for flowable substances preferably includes a squeezable container including a sealed proximal end, a sealed distal end having a threaded dispensing neck and a breakable seal, and an outer wall extending between the sealed proximal end and the sealed distal end that surrounds a storage reservoir of the squeezable container that holds a flowable substance.

In one embodiment, the delivery system may have a container support frame assembled with the squeezable container, the container support frame having a proximal edge secured to the sealed proximal end of the squeezable container, a distal edge secured to the threaded dispensing neck of the squeezable container, and first and second lateral edges extending between the proximal and distal edges and overlying opposing sides of the squeezable container. In one embodiment, the proximal and distal edges and the first and second lateral edges of the container support frame define a central opening of the container support frame that provides access to the outer wall of the squeezable container. In one embodiment, the container support frame desirably includes an elongated handle that extends proximally from the proximal edge of the container support frame.

In one embodiment, the delivery system preferably includes a dispensing cap having a proximal end coupled with the threaded dispensing neck of the squeezable container. In one embodiment, the dispensing cap preferably includes a distal end with a dispensing aperture and a dispensing cap flow channel that extends proximally from the dispensing aperture.

In one embodiment, a piercer is disposed inside the dispensing cap. In one embodiment, the piercer preferably has a proximal end with a sharpened surface. In one embodiment, the dispensing cap is rotatable relative to the threaded dispensing neck of the squeezable container for moving the dispensing cap proximally, which, in turn, slides the piercer proximally for piercing the breakable seal with the sharpened surface of the piercer.

In one embodiment, a delivery system preferably includes a porous filter impregnated with a chemical initiator. In one embodiment, the filter is desirably disposed inside the dispensing cap between a proximal end of the dispensing cap flow channel and a distal end of the piercer.

In one embodiment, the piercer may have a piercer flow channel that extends between the proximal and distal ends of the piercer. In one embodiment, the piercer flow channel is in axial alignment with the filter and the dispensing cap flow channel.

In one embodiment, a delivery system desirably includes a connector having a proximal end with female threads that are threaded onto the external threads of the dispensing neck. In one embodiment, the connector desirably has a distal end with a male luer fitting having external threads and a connector flow channel located inside the male luer fitting.

In one embodiment, the dispensing cap preferably has a proximal end including a female luer fitting that matches the male luer fitting of the connector. In one embodiment, the dispensing cap may have female threads that mesh with the external threads of the male luer fitting of the connector.

In one embodiment, the porous filter impregnated with a chemical initiator is preferably disposed within the connector flow channel adjacent a proximal end of the dispensing cap flow channel. In one embodiment, the porous filter is desirably configured to slide inside the connector flow channel.

In one embodiment, the piercer is preferably disposed within the connector flow channel of the connector and is configured to slide inside the connector flow channel. In one embodiment, the dispensing cap is rotatable about the external threads of the male luer fitting of the connector for moving the dispensing cap proximally, which, in turn, slides the porous filter proximally through the connector flow channel, which, in turn, slides the piercer proximally through the connector flow channel for piercing the breakable seal with the sharpened surface of the piercer.

In one embodiment, the elongated handle preferably includes an elongated blade having a proximal end with a rounded surface. In one embodiment, the elongated blade has flat top and bottom surfaces that extend between the proximal edge of the container support frame and the rounded surface of the elongated blade. In one embodiment, the flat top surface of the elongated blade preferably has markings (e.g., lines and numbers) for measuring distances, such as the length of a wound to be sealed using a skin adhesive.

In one embodiment, a delivery system for dispensing and applying flowable substances such as skin adhesives preferably includes a squeezable container having a sealed proximal end, a sealed distal end having a threaded dispensing neck and a breakable seal, and an outer wall extending between the sealed proximal end and the sealed distal end. In one embodiment, the outer wall preferably surrounds a storage reservoir containing a flowable substance.

In one embodiment, a delivery system may have a container support frame assembled with the squeezable container, the container support frame having a proximal edge secured to the sealed proximal end of the squeezable container, a distal edge secured to the dispensing neck of the squeezable container, and first and second lateral edges extending between the proximal and distal edges and overlying opposing sides of the squeezable container. In one embodiment, the proximal and distal edges and the first and second lateral edges of the container support frame preferably define a central opening of the container support frame that provides access to the outer wall of the squeezable container. In one embodiment, the container support frame desirably includes an elongated blade extending proximally from the proximal edge.

In one embodiment, a delivery system desirably has a connector having with a proximal end having female threads that are threaded onto the external threads of the dispensing neck of the squeezable container. In one embodiment, the connector preferably has a distal end with a male luer fitting having external threads and a connector flow channel located inside the male luer fitting.

In one embodiment, a delivery system preferably includes a dispensing cap having a proximal end including a female luer fitting that matches the male luer fitting of the connector. In one embodiment, the dispensing cap desirably has female threads that mesh with the external threads of the male luer fitting. In one embodiment, the dispensing cap may have a distal end with a dispensing aperture and a dispensing cap flow channel that extends proximally from the dispensing aperture.

In one embodiment, a delivery system desirably has a porous filter impregnated with a chemical initiator that is disposed within the connector flow channel adjacent a proximal end of the dispensing cap flow channel. In one embodiment, the porous filter is configured to slide inside the connector flow channel.

In one embodiment, a delivery system desirably has a piercer disposed inside the dispensing cap and within the connector flow channel of the connector. In one embodiment, the piercer is proximal to the porous filter and has a proximal end with a sharpened surface. In one embodiment, the female threads of the dispensing cap are rotatable about the external threads of the male luer fitting of the connector for moving the dispensing cap proximally, which, in turn, slides the porous filter proximally, which, in turn, slides the piercer proximally for piercing the breakable seal with the sharpened surface of the piercer.

In one embodiment, the elongated blade of the container support frame preferably has a proximal end with a rounded surface. In one embodiment, the elongated blade desirably has top and bottom surfaces that are flat and that extend between the proximal edge of the container support frame and the rounded surface of the elongated blade. In one embodiment, the elongated blade preferably has markings provided on one or more of the top and bottom surfaces for measuring distances.

In one embodiment, the piercer may have a piercer flow channel that is in axial alignment with the connector flow channel, the porous filter, the dispensing cap flow channel, and the dispensing aperture. In one embodiment, after the breakable seal has been pierced, the outer wall of the squeezable container may be compressed, collapsed and/or squeezed for forcing the flowable substance through the piercer flow channel, the connector flow channel, the filter, the dispensing cap flow channel, and the dispensing aperture.

In one embodiment, the dispensing cap may have a ring shaped groove that surrounds the dispensing cap flow channel and that has an open end that faces toward the proximal end of the dispensing cap for seating a distal end of the male luer fitting of the connector within the ring shaped groove.

These and other preferred embodiments of the present patent application will be described in more detail below.

DETAILED DESCRIPTION OF PREFERRED EMBODIMENTS

Figure 1:
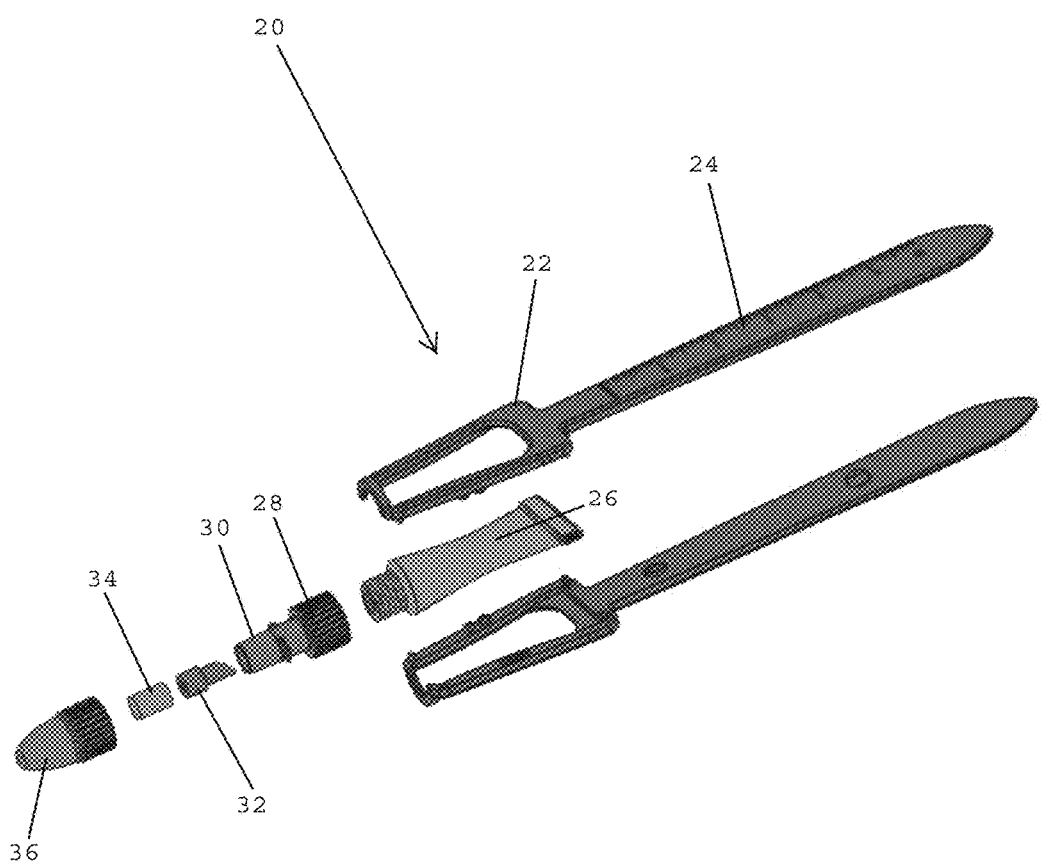
FIG. 1 shows an exploded view of a delivery system for flowable substances including a container support frame having an elongated handle, a squeezable container, a connector, a piercer, a filter, and a dispensing cap, in accordance with one embodiment of the present patent application.

Referring to FIG. 1, in one embodiment, a delivery system 20 for dispensing flowable substances preferably includes a container support frame 22 having an elongated handle 24 and a squeezable container 26 (e.g., an adhesive tube) that is assembled with the container support frame 22. In one embodiment, the delivery system 20 desirably includes a connector 28 that is threaded onto a distal end of the squeezable container 26. In one embodiment, the connector 28 includes a male luer fixture 30 that defines a connector flow channel adapted to receive a piercer 32 and a filter 34. In one embodiment, the delivery system desirably includes a dispensing cap 36 that is assembled with the male luer fixture 30 of the connector 28.

In one embodiment, the piercer 32 and the filter 34 may have cylindrical shaped bodies that are adapted to slide inside the male luer fixture 30 of the connector 28. In one embodiment, the filter 34 may be impregnated with an initiator or accelerator of polymerization of an adhesive.

Figure 2A:
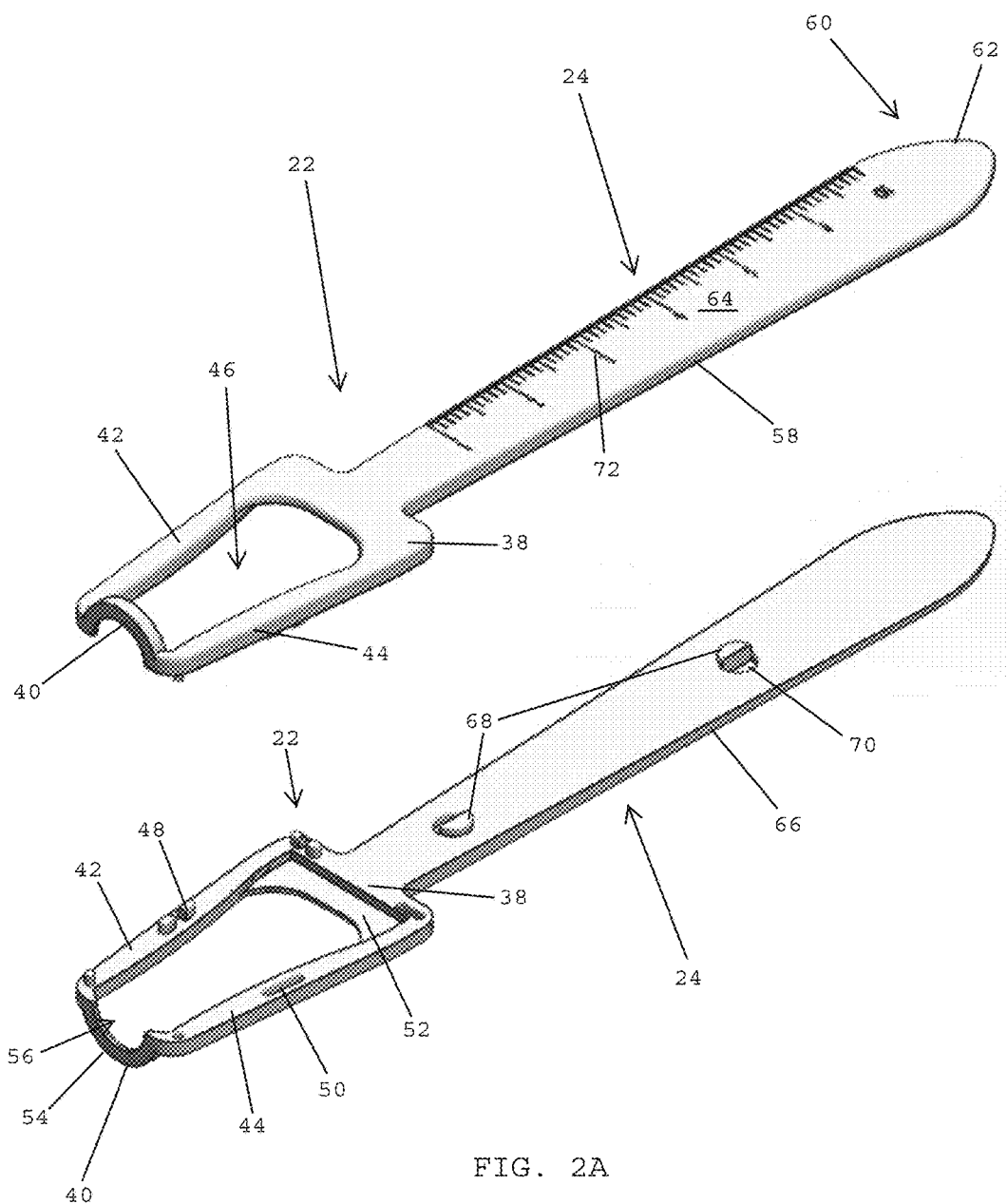
FIG. 2A shows an exploded view of the container support frame having the elongated handle shown in FIG. 1.
Figure 2B:
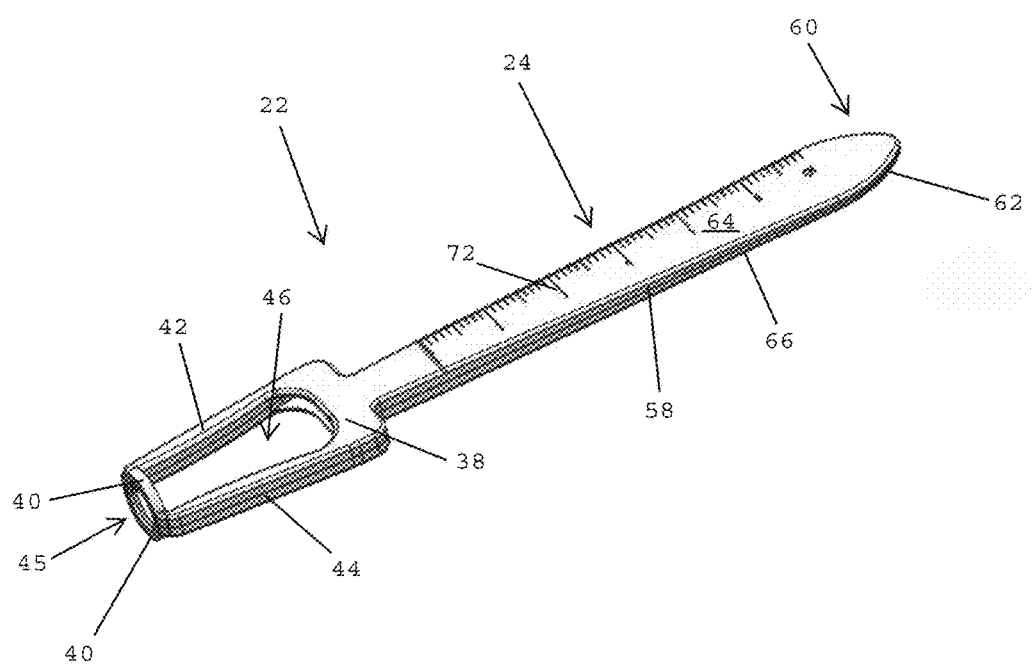
FIG. 2B shows an assembled container support frame, in accordance with one embodiment of the present patent application.

FIG. 2A shows an exploded view of the container support frame 22 having two halves that are preferably assembled together into a unitary structure, such as by welding or snap fit connections. FIG. 2B shows the container support frame 22 after the two halves have been assembled together. In one embodiment, the squeezable container may be sandwiched between the two halves of the container support frame. Referring to FIGS. 2A and 2B, in one embodiment, the container support frame 22 desirably includes a proximal edge 38, a distal edge 40 and first and second lateral edges 42, 44 extending between the proximal and distal edge 38, 40. In one embodiment, when the squeezable container 26 (FIG. 1) is assembled with the container support frame 22, the proximal and distal edges 38, 40 and the first and second lateral edges 42, 44 define a central opening 46 therebetween that preferably provides access to the compressible side walls of the squeezable container 26 for compressing the squeezable container with fingers for dispensing a substance stored in the squeezable container.

Referring to FIG. 2A, in one embodiment, the container support frame 22 preferably has two parts that are mirror images of one another and that are assembled together to provide a unitary structure. In one embodiment, the opposing edges 38, 40, 42, and 44 may include projections 48 and depressions 50 that enable the two parts of the container support frame to be snap-fit, welded and/or assembled together.

In one embodiment, the container support frame 22 may have a proximal trough 52 adjacent the proximal edge 38 that is adapted to receive a sealed proximal end of the squeezable container 26 (FIG. 1), such as a folded and sealed tail of a squeezable container as will be described in more detail herein. In one embodiment, the distal edge 40 of the container support frame preferably includes a bridge 54 defining a C-shaped opening 56 that extends between the distal ends of the first and second lateral edges 42, 44. Referring to FIG. 2B, in one embodiment, when the two parts of the container support frame 22 are assembled together, the C-shaped openings cooperatively define a circular opening 45 at the distal edge 40 that is adapted to receive and support a dispensing neck of the squeezable container 26 (FIG. 1) as will be described in more detail herein.

Referring to FIGS. 2A and 2B, in one embodiment, the container support frame 22 desirably includes an elongated handle 24 that extends proximally from the proximal edge 38 of the support frame. In one embodiment, the elongated handle 24 preferably defines an elongated blade 58 having a proximal end 60 with a rounded surface 62 that may be utilized for spreading a substance such as a topical skin adhesive used during medical procedures for closing wounds. In one embodiment, the elongated blade 58 preferably includes a flat top surface 64 and a flat bottom surface 66. In one embodiment, the elongated blade 58 has two parts that are snap-fit together using projections 68 and depressions 70 molded into opposing faces of the two elongated blade parts. In one embodiment, the top surface 64 of the elongated blade 58 preferably includes ruler markings 72 provided thereon so that the elongated blade 58 may be used for measuring distances such as the length of a wound opening.

Providing a container support frame with a proximally extending handle enables a user to hold the delivery system like a pencil or pen with the thumb and fingers free to engage the compressible side walls of the squeezable container while the area of the hand between the thumb and the index finger cradles the elongated handle to provide for improved ergonomics and control of the delivery system.

In one embodiment, the squeezable container is positioned over the central opening 46 of the container support frame with a sealed tail disposed within the trough 52 and a dispensing neck disposed within a C-shaped opening 56 defined by the distal edge 40 of the container support frame 22. The other half of the container support frame may be positioned atop the squeezable container and the opposing projections 48, 68 and grooves 50, 70 on the two halves of the frame may be utilized to snap-fit the two halves of the container support frame 22 together. In one embodiment, the two halves of the container support frame 22, including the proximal and distal edges 38, 40 and the first and second lateral edges 42, 44, are snap-fit together to form an assembled distal end of the container support frame 22, and the two parts of the elongated handle 24 are snap-fit together to form an assembled proximal end of the container support frame 22.

Figure 3A:
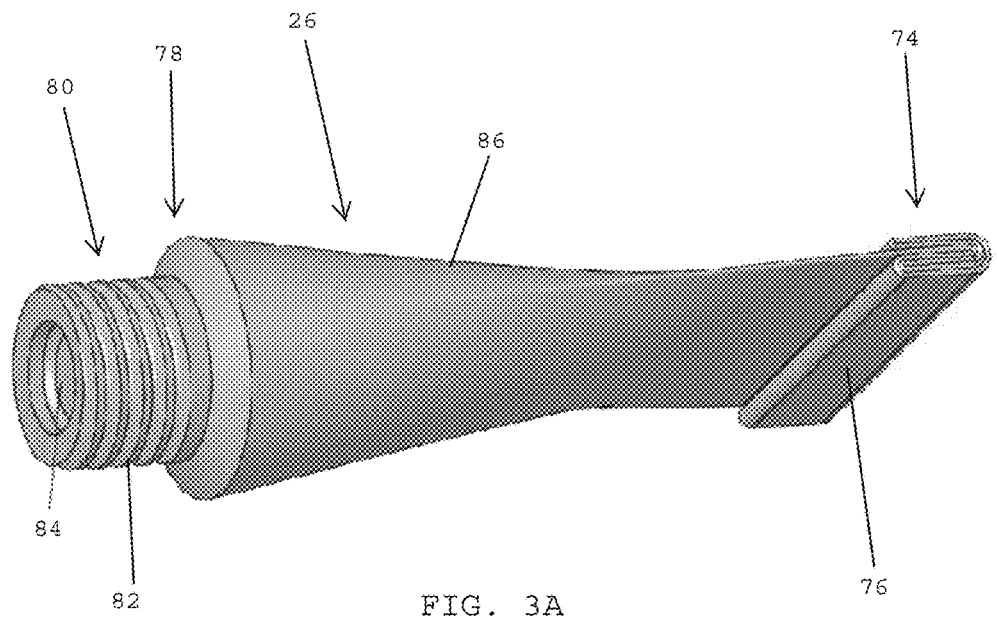
FIG. 3A shows a perspective view of the squeezable container shown in FIG. 1.
Figure 3B:
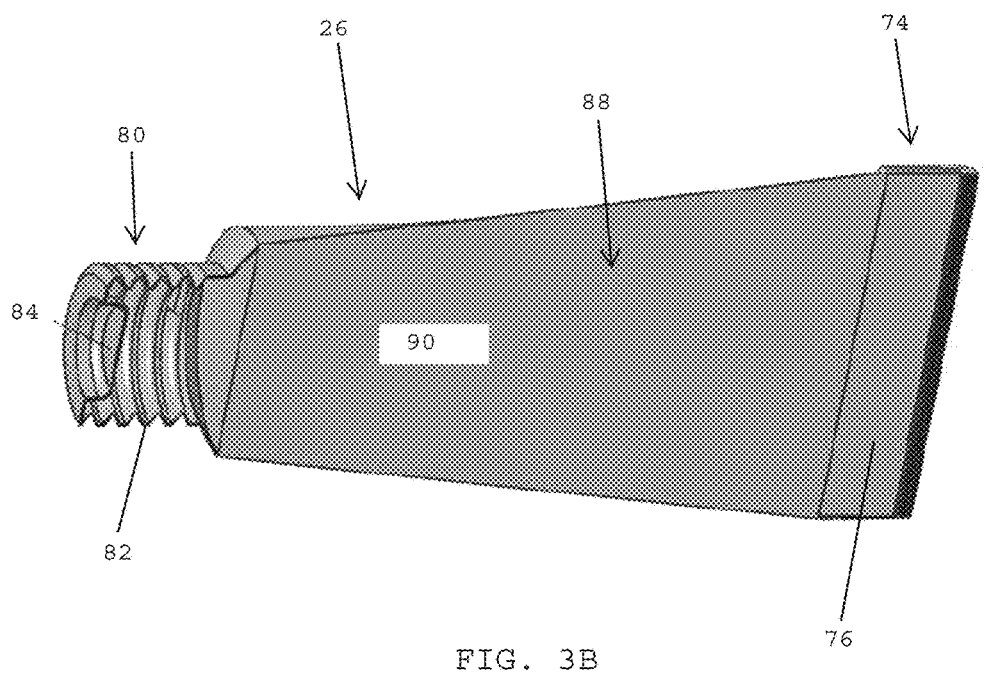
FIG. 3B shows a cross-sectional view of the squeezable container shown in FIG. 1.

Referring to FIGS. 3A and 3B, in one embodiment, the squeezable container 26 (FIG. 1) preferably includes a sealed proximal end 74 having a folded over, sealed tail 76 and a sealed distal end 78 including a dispensing neck 80 having external threads 82 and a breakable seal 84 disposed inside the dispensing neck 80. In one embodiment, the squeezable container 26 preferably includes a compressible outer wall 86 that extends between the sealed proximal end 74 and the sealed distal end 78. The outer wall 86 preferably defines a storage reservoir 88 of the squeezable container 26 that contains a flowable substance 90, such as a topical skin adhesive used for closing wounds.

In one embodiment, the folded over, sealed tail 76 desirably extends along a proximal end of the squeezable container 26. The tail may have one or more flat surfaces that extend laterally at the proximal end of the squeezable container. In one embodiment, the folded over, sealed tail 76 is adapted to be positioned within the proximal trough 52 adjacent the proximal edge 38 of the container support frame 22 (FIG. 2A). When the container support frame is assembled, the two halves of the frame may pinch the sealed tail 76 for securely holding the squeezable container in place and for preventing the proximal end of the squeezable container from leaking. In one embodiment, the proximal edge of the container support frame may clamp, compress and/or pinch the sealed tail 76 of the squeezable container to prevent the sealed tail from unfurling, becoming unsealed, opening, and/or leaking during manufacture, assembly, transport, storage or use of the delivery systems disclosed herein In one embodiment, the breakable seal 84 is disposed within the dispensing neck 80 at the sealed distal end 78 of the squeezable container 26. In one embodiment, the breakable seal 84 may be pierced or broken so that the flowable substance 90 within the squeezable container 26 may be dispensed through the dispensing neck 80 at the distal end 78 of the squeezable container 26.

When the squeezable container 26 is assembled with the container support frame 22, the dispensing neck 80 preferably passes through the opposing C-shaped openings defined by the distal edge 40 of the container support frame 22 (FIG. 2A). The opposing C-shaped openings may define a circular opening with the dispensing neck passing through the circular opening.

Figures 4A, 4B:
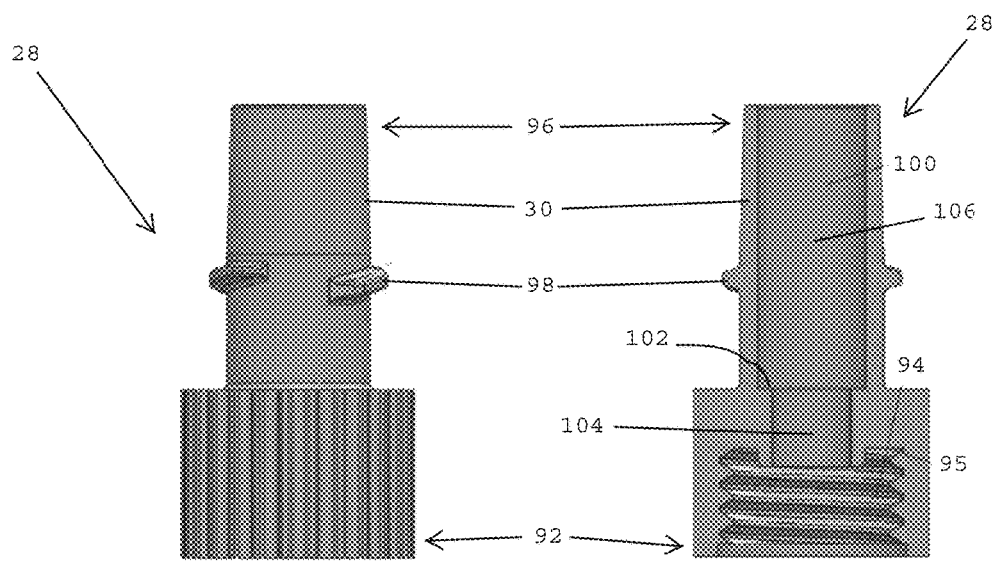
FIG. 4A shows a side view of the connector shown in FIG. 1.
FIG. 4B shows a cross-sectional view of the connector shown in FIG. 4A.

Referring to FIGS. 4A, and 4B, in one embodiment, a delivery system for dispensing a flowable substance preferably includes the connector 28 having a proximal end 92 with female threads 94 that are adapted to be threaded onto the external threads 82 of the dispensing neck 80 of the squeezable container 26 (FIG. 3B). The connector 28 desirably includes a distal end 96 with the male luer fixture 30 extending to the distal end 96. The male luer fixture 30 preferably has external threads 98 provided thereon. In one embodiment, the male luer fixture 30 defines a connector flow channel 100 that extends between the female threads 94 at the proximal end 92 and the distal end 96 of the male luer fitting 30. In one embodiment, the connector flow channel 100 may have a connector flow channel shoulder 102 that divides the connector flow channel 100 into a proximal flow channel section 104 having a smaller diameter and a distal flow channel section 106 having a larger diameter. As will be described in more detail herein, the connector flow channel shoulder 102 desirably provides a hard stop for the piercer 32 (FIG. 1) as the piercer moves proximally for piercing the breakable seal 84 (FIG. 3B) of the squeezable container.

Figures 5A, 5B:
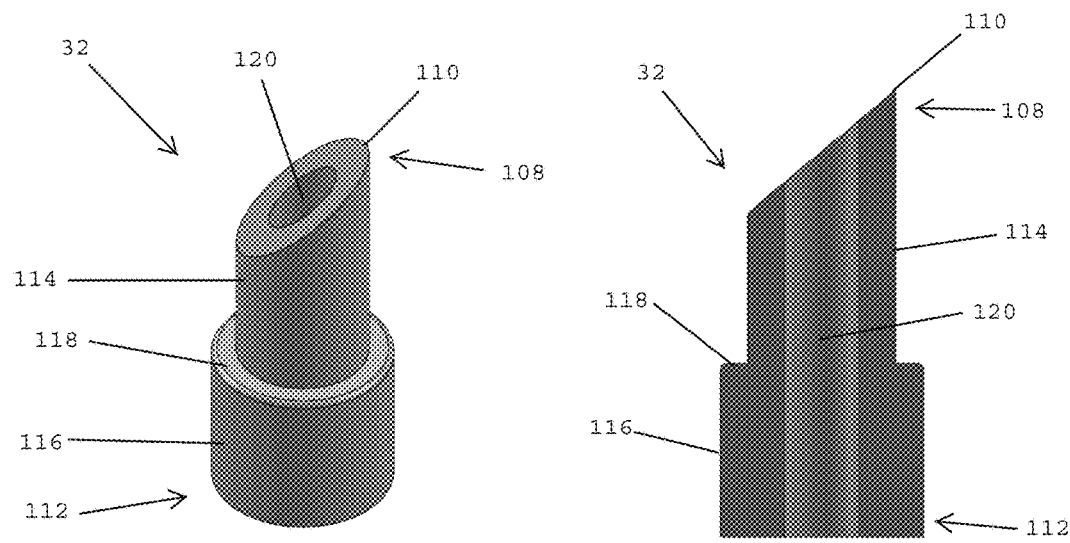
FIG. 5A shows a perspective view of the piercer shown in FIG. 1.
FIG. 5B shows a cross-sectional view of the piercer shown in FIG. 5A.

Referring to FIGS. 5A and 5B, in one embodiment, the piercer 32 preferably has a proximal end 108 with a sharpened surface 110 and a distal end 112 that is opposite the proximal end 108. The piercer 32 desirably includes a smaller outer diameter section 114 adjacent the proximal end 108 and a larger outer diameter section 116 adjacent the distal end 112. A piercer shoulder 118 preferably divides the smaller outer diameter proximal section 114 from the larger outer diameter distal section 116. In one embodiment, the piercer 32 includes a piercer flow channel 120 that preferably extends between the proximal end 108 and the distal end 114 thereof for allowing the flowable substance to pass through the piercer.

In one embodiment, when the piercer 32 is assembled with the connector 28, the piercer shoulder 118 preferably opposes the connector flow channel shoulder 102 (FIG. 4B). In one embodiment, as the piercer 32 moves proximally, the shoulder 118 on the piercer 32 eventually contacts the connector flow channel shoulder 102 (FIG. 4B) to provide a hard stop for halting proximal movement of the piercer within the connector flow channel 100 of the connector 28 (FIG. 4B). The hard stop preferably engages the piercer after the sharpened surface 110 of the piercer has broken the seal.

Referring to FIGS. 1 and 4A-4B, in one embodiment, the piercer 32 is positioned within the connector flow channel 100 defined by the male luer fixture 30 of the connector. In one embodiment, the proximal end 108 of the piercer 32 faces toward the proximal end 92 of the connector 28. In one embodiment, the filter 34 is also positioned within the connector flow channel 100 defined by the male luer fixture 30. The filter 34 is preferably distal to the piercer 32.

Figure 6A:
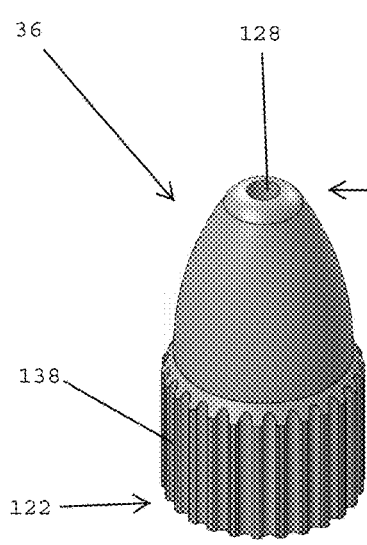
FIG. 6A shows a perspective view of the dispensing cap shown in FIG. 1.
Figure 6B:
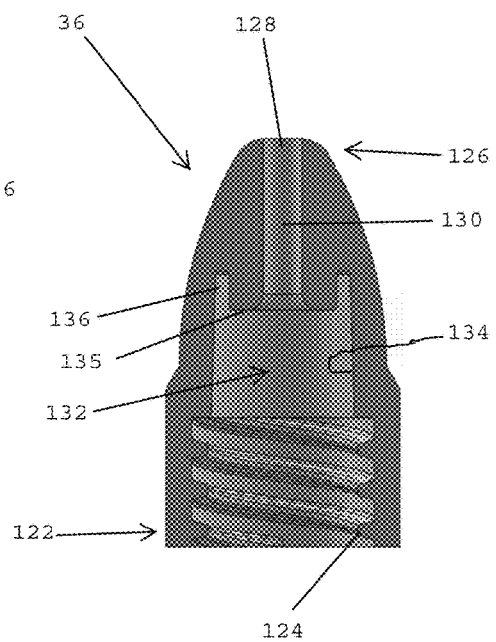
FIG. 6B shows a cross-sectional view of the dispensing cap shown in FIG. 6A.

Referring to FIGS. 6A and 6B, in one embodiment, the delivery system for dispensing a flowable substance preferably includes a dispensing cap 36 having a proximal end 122 with female threads 124 and a distal end 126 having a dispensing aperture 128. In one embodiment, the dispensing cap 36 preferably includes a dispensing cap flow channel 130 that extends proximally from the dispensing aperture 128 at the distal end 126 thereof.

In one embodiment, the dispensing cap 36 is a hollow body that defines a dispensing cap chamber 132 that is adapted to receive the distal end 96 of the male luer fitting 30 of the connector 28 (FIGS. 4A and 4B). In one embodiment, the dispensing cap chamber 132 has side walls 134 that define a female luer fixture that is adapted to receive the male luer fixture 30 of the connector 28 (FIGS. 4A and 4B). In one embodiment, a distal end of the dispensing cap chamber 132 has a distal end wall 135 having a ring-shaped groove 136 formed therein for seating a distal-most end of the male luer fixture 30 (FIGS. 4A and 4B). In one embodiment, the luer connection between the dispensing cap and the connector prevents leaking of the flowable substance as it is being dispensed by the delivery system disclosed herein.

In one embodiment, an outer surface of the dispensing cap 36 preferably includes a knurled surface 138 or a roughened surface for enabling an operator to rotate the dispensing cap relative to the connector. In one embodiment, the knurled surface 138 is located adjacent the proximal end 122 of the dispensing cap 36. The distal end of the dispensing cap may have a smooth, dome shaped outer surface that that tapers inwardly to the dispensing aperture 128.

In one embodiment, the dispensing cap is assembled with the connector so that the female threads 124 of the dispensing cap 36 mesh with the external threads 98 of the male luer fixture 30. In one embodiment, as the dispensing cap 36 is rotated, the female threads 124 of the dispensing cap 36 mesh with the external threads 98 of the male luer fixture 30 to move the dispensing cap 36 in a proximal direction toward the proximal end 92 of the connector 28.

Figure 7A:
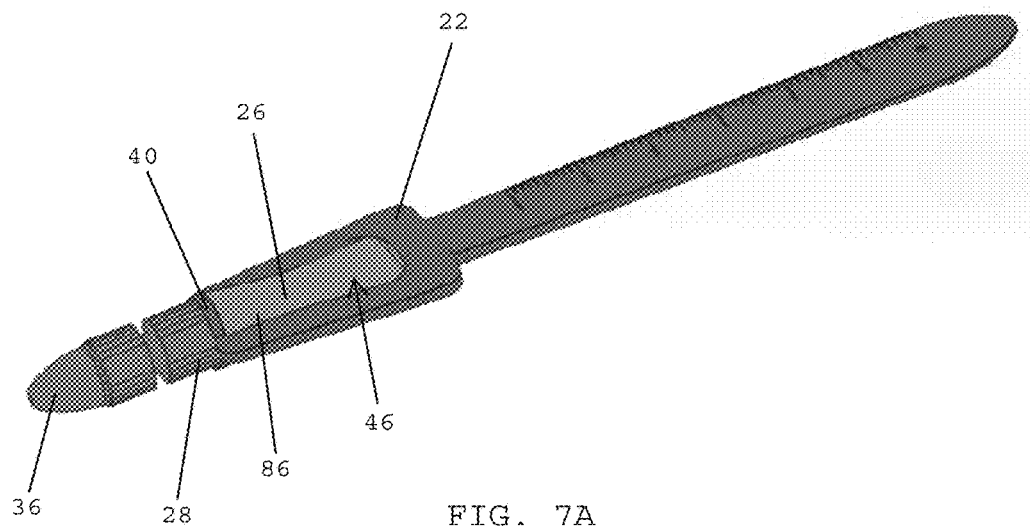
FIG. 7A shows a delivery system including a squeezable container assembled with a container support frame, in accordance with one embodiment of the present patent application.
Figure 7B:
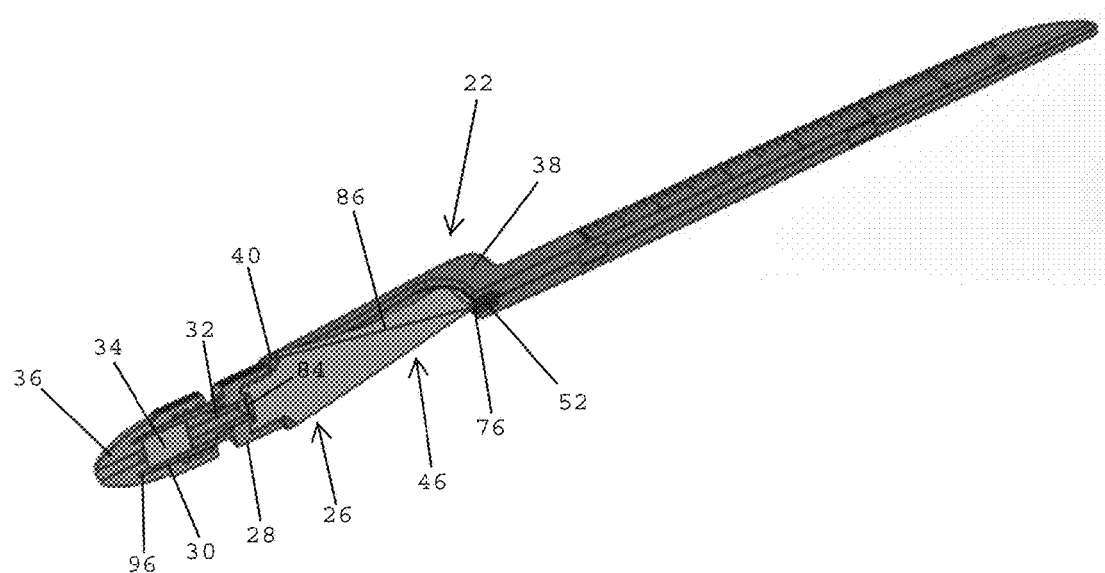
FIG. 7B shows a cross-sectional view of the delivery system shown in FIG. 7A.

Referring to FIGS. 7A and 7B, in one embodiment, the squeezable container 26 is preferably assembled with the connector support frame 22 so that the outer wall 86 of the squeezable container 26 is aligned with and accessible through the central opening 46 of the container support frame 22. In one embodiment, top and bottom major surfaces of the compressible outer wall 86 of the squeezable container 26 are accessible through the central opening 46 so that the squeezable container 26 may be engaged by fingers from both the top side and the bottom side of the squeezable container. In one embodiment, the folded over, sealed tail 76 at the proximal end of the squeezable container 26 is secured within the proximal trough 52 defined by the opposing inner surfaces of the proximal edge 38. The externally threaded dispensing neck 80 at the distal end 78 of the squeezable container 26 is preferably secured within the circular opening defined by the distal edge 40 of the container support frame 22.

In one embodiment, the female threads of the connector 28 are threaded onto the external threads of the dispensing neck 80. The piercer 32 is preferably positioned within the connector flow channel defined by the male luer fixture 30 of the connector and the filter 34 is positioned inside the male luer fixture 30 at a position that is distal to the piercer 32. The sharpened edge 110 at the proximal end of the piercer 32 preferably opposes the breakable seal 84 of the squeezable container 26.

In one embodiment, the dispensing cap 36 is assembled with the male luer fixture 30 so that the female threads of the dispensing cap 36 mesh with the external threads of the male luer fixture. In one embodiment, the distal most end 96 of the male luer fixture 30 is aligned with the ring-shaped groove 136 formed in the distal end wall 135 of the dispensing cap chamber 132 (FIG. 6B).

Figure 8:
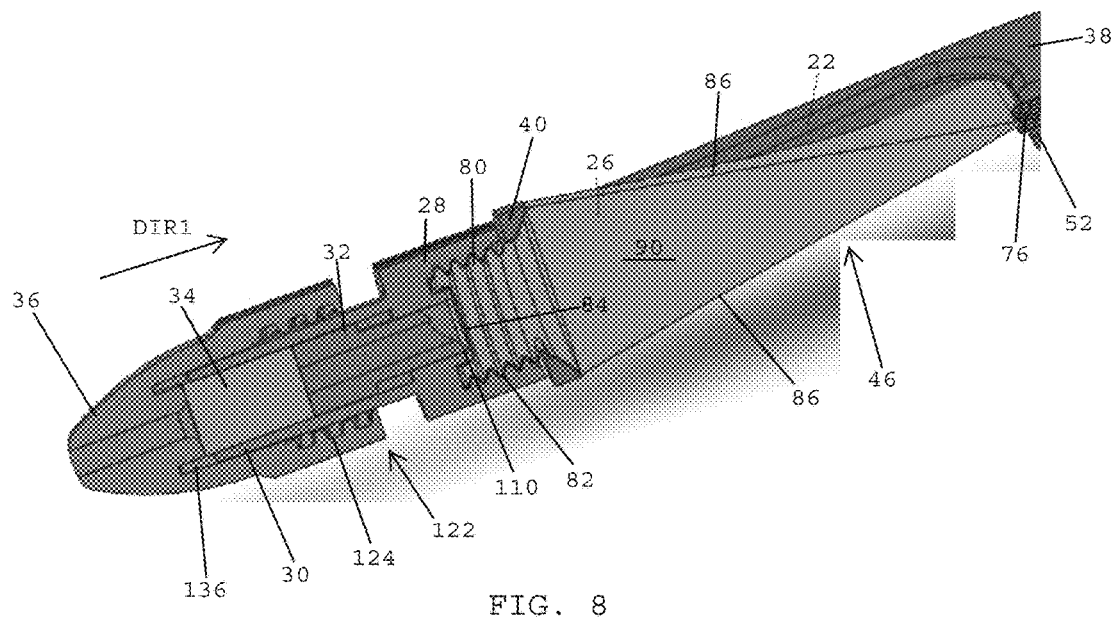
FIG. 8 shows the delivery system of FIGS. 7A and 7B prior to breaking a seal of the squeezable container.

FIG. 8 shows the delivery system with the connector 28 and the dispensing cap 36 assembled with the distal end of the squeezable container 26, but prior to breaching the breakable seal 84 of the squeezable container 26. In one embodiment, the female threads at the proximal end of the connector 28 are threaded onto the external threads 82 of the dispensing neck 80 of the squeezable container 26. In one embodiment, the folded over sealed tail 76 is secured (e.g., wedged or pinched) within the proximal trough 52 adjacent the proximal edge 38 of the container support frame 22 for securely affixing the squeezable container to the container support frame 22 and to prevent leakage from the proximal end of the squeezable container. The outer wall 86 of the squeezable container 26 is preferably accessible through the central opening 46 of the container support frame 22. The dispensing neck 80 of the squeezable container 26 is preferably secured within the circular opening defined by the distal edge 40 of the container support frame. In one embodiment, the distal edge 40 preferably forms a snug fit (e.g., a friction fit) with the outer surface of the dispensing neck 80 so that the distal end of the squeezable container 26 does not shift and/or move during use of the delivery system disclosed herein.

In one embodiment, the piercer 32 is preferably disposed within the connector flow channel defined by the male luer fixture 30 of the connector 28. The sharpened point 110 at the proximal end of the piercer 32 preferably opposes the breakable seal 84 of the squeezable container 26. The filter 34 containing a chemical initiator for the flowable substance 90 is preferably positioned within the connector flow channel at a location that is distal to a distal end of the piercer 32.

In one embodiment, the proximal end 122 of the dispensing cap 36 is preferably aligned with the distal end of the male luer fixture 30 so that the dispensing cap 36 may be assembled with the distal end of the connector 28. In one embodiment, the dispensing cap 36 is advanced proximally so that the distal end of the male luer fixture 30 is juxtaposed with the ring-shaped groove 136 formed in the distal end wall 135 of the dispensing cap chamber 132 (FIG. 6B). At the same time, the female threads 124 of the dispensing cap 36 may begin to mesh with the external threads 98 provided on the outer surface of the male luer fixture 30.

At the stage shown in FIG. 8, the connector 28 is fully threaded onto the externally threaded dispensing neck 80 of the squeezable container 26. The breakable seal 84 remains unbroken and the sharpened point 110 at the proximal end of the piercer 32 is distal to the breakable seal 84. In one embodiment, once the female threads 124 of the dispensing cap 36 engaged with the external threads 98 on the male luer fixture 30 of the connector 28, further rotation of the dispensing cap 36 relative to the connector 28 will move the dispensing cap 36 in the proximal direction designated DIR1.

Figure 9:
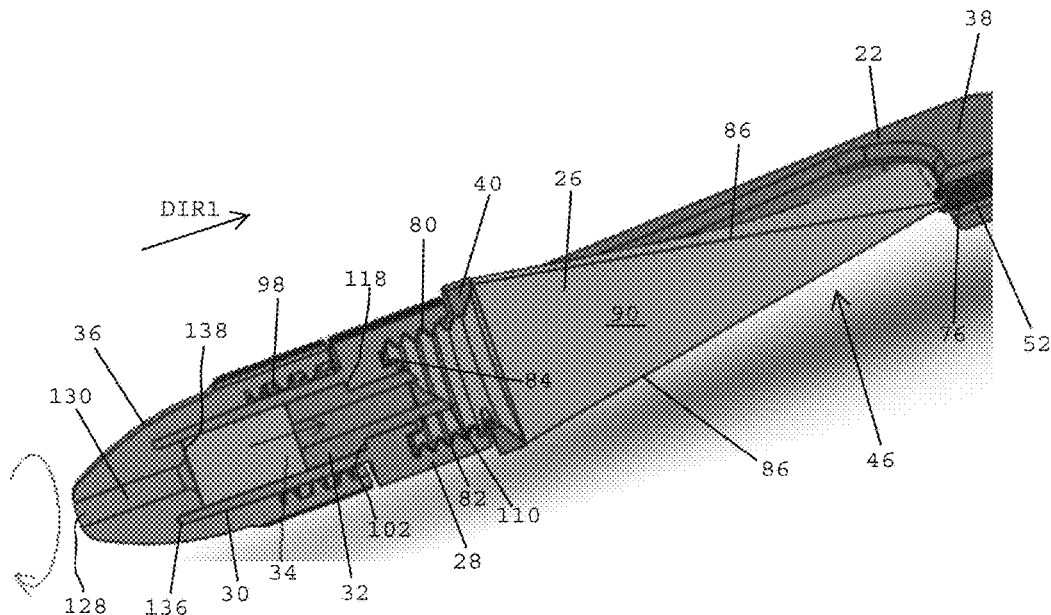
FIG. 9 shows the delivery system of FIG. 8 after breaking the seal of the squeezable container.

FIG. 9 shows the dispensing cap 36 after it has been rotated relative to the connector 28. In one embodiment, as the dispensing cap 36 is rotated, the dispensing cap 36 moves in the proximal direction designated DIR1. The distal end wall 135 of the dispensing cap chamber 132 (FIG. 6B) preferably abuts against a distal end of the filter 34 which moves the filter 34 in the proximal direction DIR1. As the filter 34 moves proximally, the filter, in turn, engages a distal end of the piercer 32 for moving the piercer proximally so that the sharpened point 110 of the piercer 32 breaks the seal 84 at the distal end of the squeezable container 26. Proximal movement of the piercer is halted when the piercer shoulder 118 (FIG. 5B) engages the connector shoulder 102 (FIG. 4B) provided inside the male luer fixture 30. In one embodiment, proximal movement of the dispensing cap 36 may also be halted when the distal-most end of the male luer fixture 30 bottoms out within the ring-shaped groove 136 formed in the distal end wall of the dispensing cap chamber of the dispensing cap.

Once the seal 84 has been broken, the outer walls 86 of the squeezable container 26 may be compressed for forcing the flowable substance 90 through the dispensing neck 80, the piercer flow channel 120, the filter 34, and the dispensing cap flow channel 130 for being dispensed from the dispensing aperture 128. The flowable substance may react with a chemical impregnated in the filter as the flowable substance passes through the filter. The filter may be porous and may be impregnated with an initiator or accelerator of polymerization.

In one embodiment, as the dispensing cap 36 is being rotated for breaking the seal with the piercer, an operator preferably holds the squeezable container via the container support frame 22 so that an operator does not have to engage the side walls 86 of the squeezable container 26 during the unsealing stage, which could prematurely dispense the stored substance as the seal is broken. Thus, in one embodiment, the seal may be broken without physically contacting the squeezable container 26, which minimizes inadvertent and/or accident leakage of the flowable substance 90 from the dispensing neck 80. The structure disclosed herein preferably isolates the step of breaking the seal from the step of squeezing the container to dispense a flowable substance so as to minimize leakage and/or discharge of excessive amounts of flowable substances from a squeezable container.

Figure 10:
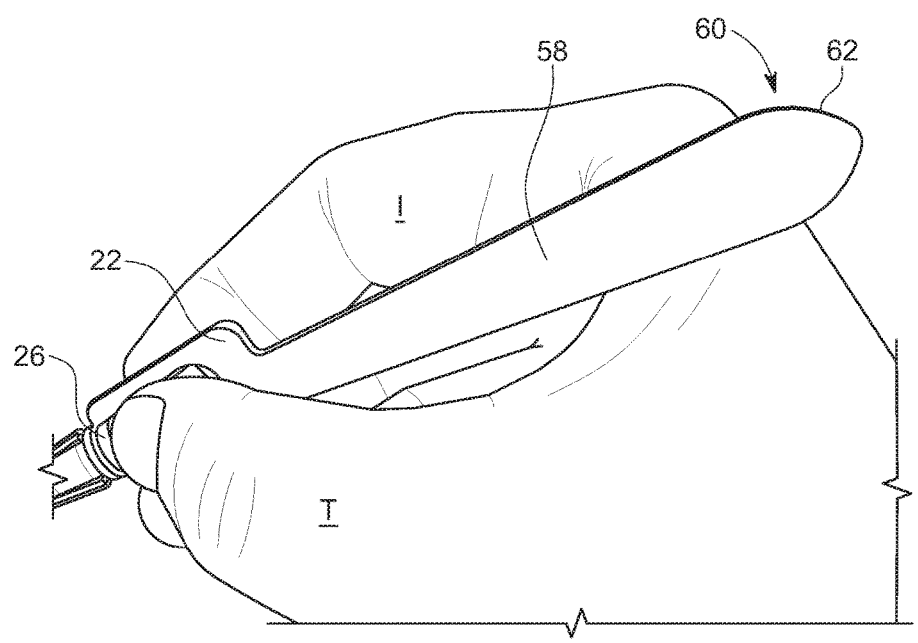
FIG. 10 shows a method of using the delivery system shown in FIGS. 8 and 9 for dispensing a flowable substance from a squeezable container, in accordance with one embodiment of the present patent application.

Referring to FIG. 10, in one embodiment, after the seal of the squeezable container 26 has been broken, the container support frame 22 may be utilized for accurately dispensing a flowable substance (e.g., a topical skin adhesive) at a desired location on a patient. The proximally extending blade 58 preferably enables an operator to exert enhanced control and accuracy over where the flowable substance is dispensed. In one embodiment, the elongated blade 52 may be supported against a portion of a hand that is located between a thumb T and an index finger I. Thus, the elongated blade 58 may be used to hold the delivery system like a writing tool so as to stabilize and accurately control the orientation and configuration of the container support frame 22 when dispensing the flowable substance from the squeezable container 26. In one embodiment, the rounded surface 62 at the proximal end 60 of the elongated blade 58 may be utilized for spreading adhesive that has been dispensed from the squeezable container 26. One or more external surfaces of the elongated blade 58 may include ruler markings provided thereon for measuring distances such as the length of a wound or cut that needs repair.

Figure 11:
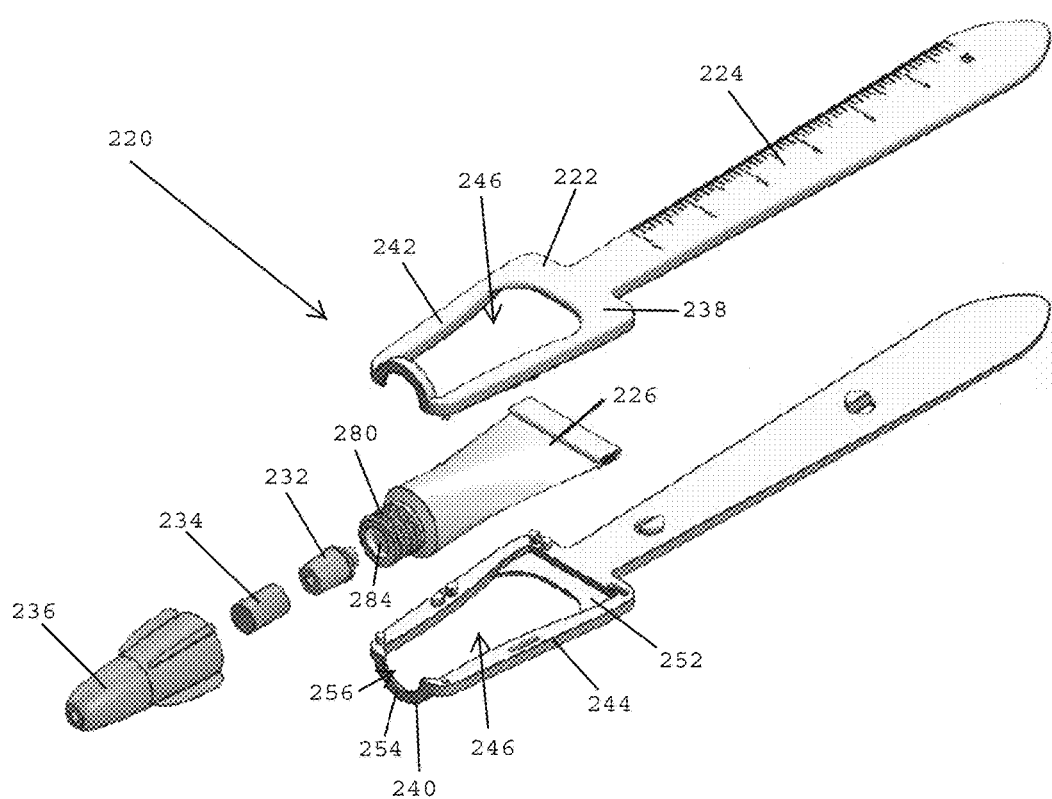
FIG. 11 shows an exploded view of a delivery system for flowable substances including a container support frame having an elongated handle, a squeezable container, a piercer, a filter, and a dispensing cap, in accordance with one embodiment of the present patent application.

Referring to FIG. 11, in one embodiment, a delivery system 220 for dispensing flowable substances preferably includes a container support frame 222 having an elongated handle 224 and a squeezable container 226 that is adapted for being assembled with the container support frame 222. In one embodiment, the delivery system 220 desirably includes a piercer 232 and a filter 234 that are disposed within a dispensing cap 236 that is adapted for being assembled with a threaded dispensing neck 280 of the squeezable container 226.

In one embodiment, the container support frame 222 desirably includes a proximal edge 238, a distal edge 240 and first and second lateral edges 242, 244 extending between the proximal and distal edges 238, 240. In one embodiment, when the squeezable container 26 (FIG. 11) is assembled with the container support frame 222, the proximal and distal edges 238, 240 and the first and second lateral edges 242, 244 define a central opening 246 therebetween that preferably provides access to the compressible side walls of the squeezable container 226 for compressing the squeezable container with fingers for dispensing a substance stored in the squeezable container.

In one embodiment, the container support frame 222 preferably has two parts that are mirror images of one another and that are assembled together to provide a unitary structure. In one embodiment, the opposing edges 238, 240, 242, and 244 may include projections 248 and depressions 250 that enable the two parts of the container support frame to be snap-fit, welded and/or assembled together.

In one embodiment, the container support frame 222 may have a proximal trough 252 adjacent the proximal edge 238 that is adapted to receive a sealed proximal end of the squeezable container 226, such as a sealed tail of a squeezable container. In one embodiment, the distal edge 240 of the container support frame preferably includes a bridge 254 defining a C-shaped opening 256 that extends between the distal ends of the first and second lateral edges 242, 244. In one embodiment, when the two parts of the container support frame 222 are assembled together, the C-shaped openings define a circular opening at the distal edge 240 that is adapted to receive and support the threaded dispensing neck 280 of the squeezable container 226.

Figures 12A, 12B:
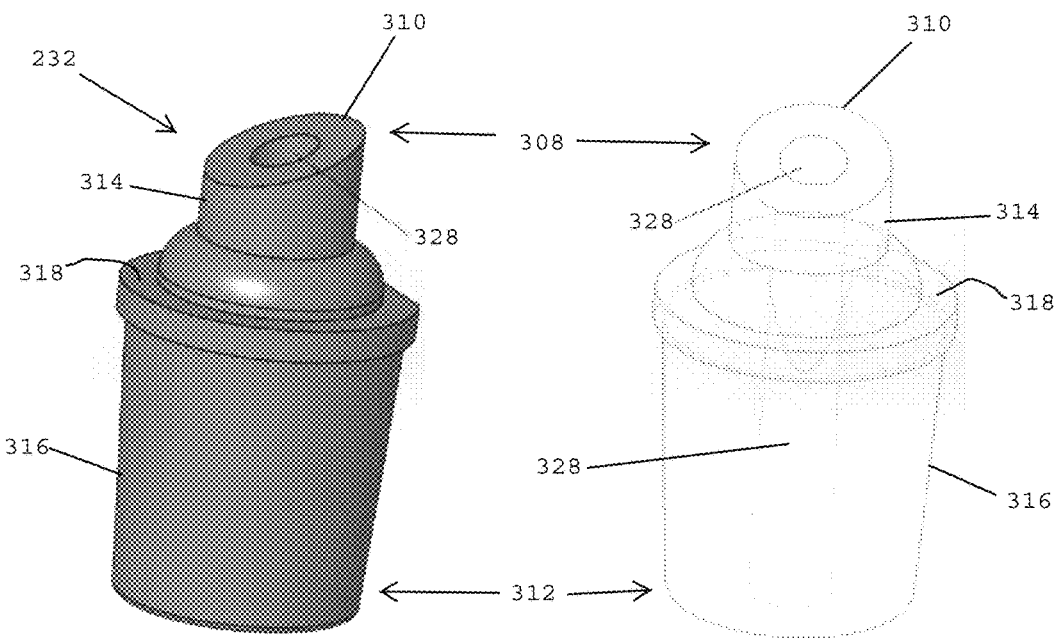
FIG. 12A shows a perspective view of the piercer shown in FIG. 11.
FIG. 12B shows a partial cross-sectional view of the piercer shown in FIG. 12A.

Referring to FIGS. 12A and 12B, in one embodiment, the piercer 232 preferably has a proximal end 308 with a sharpened surface 310 or point and a distal end 312 that is opposite the proximal end 308. The piercer 232 desirably includes a smaller outer diameter section 314 adjacent the proximal end 308 and a larger outer diameter section 316 adjacent the distal end 312. A piercer shoulder 318 preferably divides the smaller outer diameter proximal section 314 from the larger outer diameter distal section 116. In one embodiment, the piercer 32 includes a piercer flow channel 328 that preferably extends between the proximal end 308 and the distal end 314 thereof.

In one embodiment, when the piercer 232 is assembled with the squeezable container 226, the sharpened surface 310 preferably opposes a breakable seal 284 provided at the distal end of the squeezable container 226. In one embodiment, as the piercer moves proximally, the sharpened surface 310 is configured to break the seal 284 for enabling the flowable substance to be dispensed from the squeezable container.

Figures 13A, 13B:
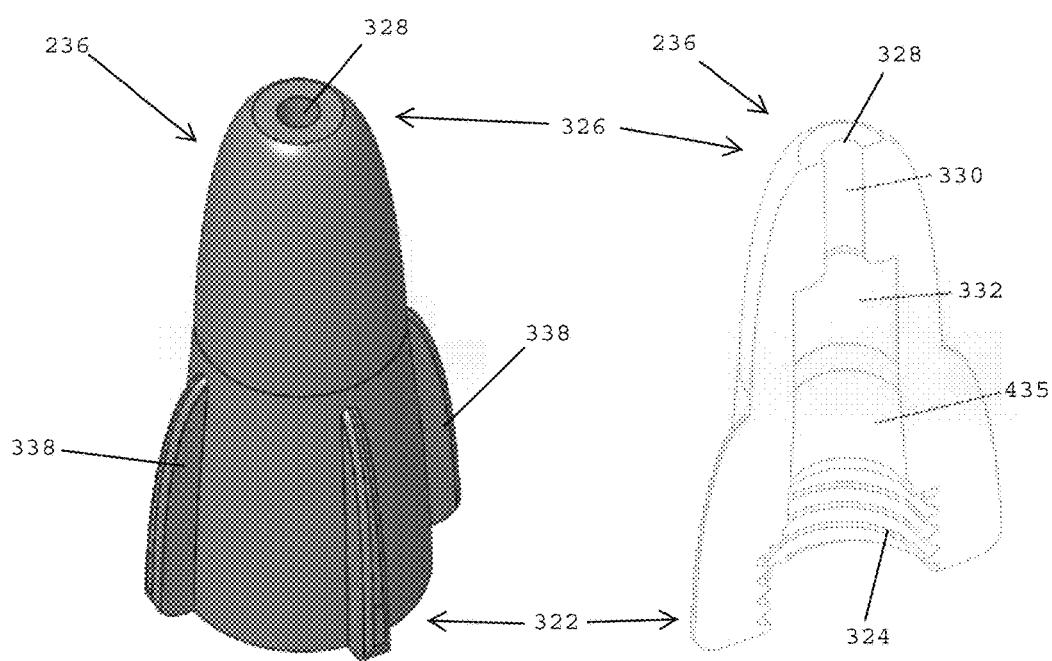
FIG. 13A shows a perspective view of the dispensing cap shown in FIG. 11.
FIG. 13B shows a cross-sectional view of the dispensing cap shown in FIG. 13A.

Referring to FIGS. 13A and 13B, in one embodiment, the delivery system for dispensing a flowable substance preferably includes a dispensing cap 236 having a proximal end 322 with female threads 324 and a distal end 326 having a dispensing aperture 328. In one embodiment, the dispensing cap 236 preferably includes a dispensing cap flow channel 330 that extends proximally from the dispensing aperture 328 at the distal end 326 thereof.

In one embodiment, the dispensing cap 226 is a hollow body that defines a filter chamber 332 that is adapted to receive the filter 234 (FIG. 11). In one embodiment, the filter chamber 332 preferably has a distal end wall 335 that is located adjacent a proximal end of the dispensing cap flow channel. In one embodiment, the dispensing cap 226 preferably has a piercer chamber 345 that is configured to receive the piercer 232 (FIG. 11). In one embodiment, the piercer chamber 345 is proximal to the filter channel 332.

In one embodiment, an outer surface of the dispensing cap 236 preferably includes one or more gripping flanges 338 for enabling an operator to rotate the dispensing cap relative to the threaded dispensing neck 280 of the squeezable container 226 (FIG. 11). In one embodiment, the one or more gripping flanges 338 may be located adjacent the proximal end 322 of the dispensing cap 236.

Figure 14:
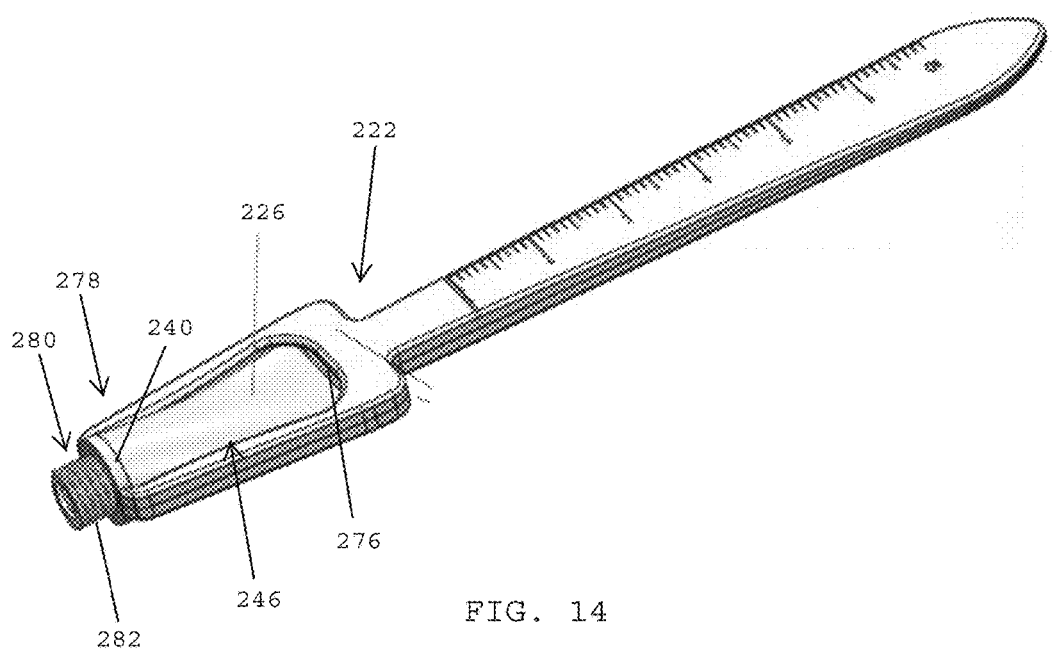
FIG. 14 shows a delivery system for flowable substance including the squeezable container and the container support frame of FIG. 11 assembled together.

Referring to FIG. 14, in one embodiment, the squeezable container 226 is preferably assembled with the connector support frame 222 so that the outer wall 286 of the squeezable container 226 is aligned with and accessible through the central opening 246 of the container support frame 222. In one embodiment, top and bottom major surfaces of the compressible outer wall 286 of the squeezable container 226 are accessible through the central opening 246 so that the squeezable container 226 may be engaged by fingers from both the top side and the bottom side of the container. In one embodiment, the folded over, sealed tail 276 at the proximal end of the squeezable container 226 is secured within the proximal trough 252 (FIG. 11) defined by the opposing inner surfaces of the proximal edge 238. The externally threaded dispensing neck 280 at the distal end 278 of the squeezable container 226 is preferably secured within the circular opening defined by the distal edge 240 of the container support frame 222.

Figure 15:
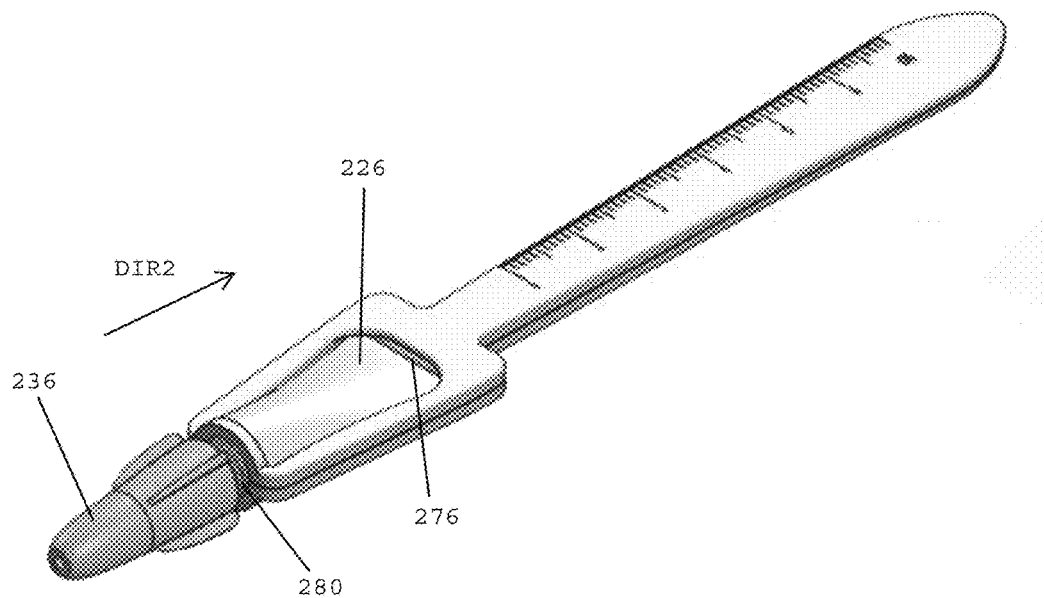
FIG. 15 shows the delivery system of FIG. 14 with a dispensing cap secured to a distal end of a squeezable container, in accordance with one embodiment of the present patent application.

Referring to FIGS. 13B, 14, and 15, in one embodiment, the dispensing cap 236 is assembled with the external threads 282 of the dispensing neck 280 of the squeezable container 226 so that the female threads 324 of the dispensing cap 236 mesh with the external threads 282 of the dispensing neck 280. In one embodiment, rotation of the female threads 324 of the dispensing cap 236 relative to the external threads 282 of the dispensing neck 280 moves the dispensing cap 236 in a proximal direction DIR2 (FIG. 15) toward the proximal end 274 of the squeezable container 326.

In one embodiment, when the female threads of the dispensing cap are threaded onto the external threads of the dispensing neck, the piercer is preferably positioned within the piercer chamber of the dispensing cap and the filter is positioned within the filter chamber of the dispensing cap. The sharpened edge at the proximal end of the piercer preferably opposes the breakable seal of the squeezable container.

Figure 16:
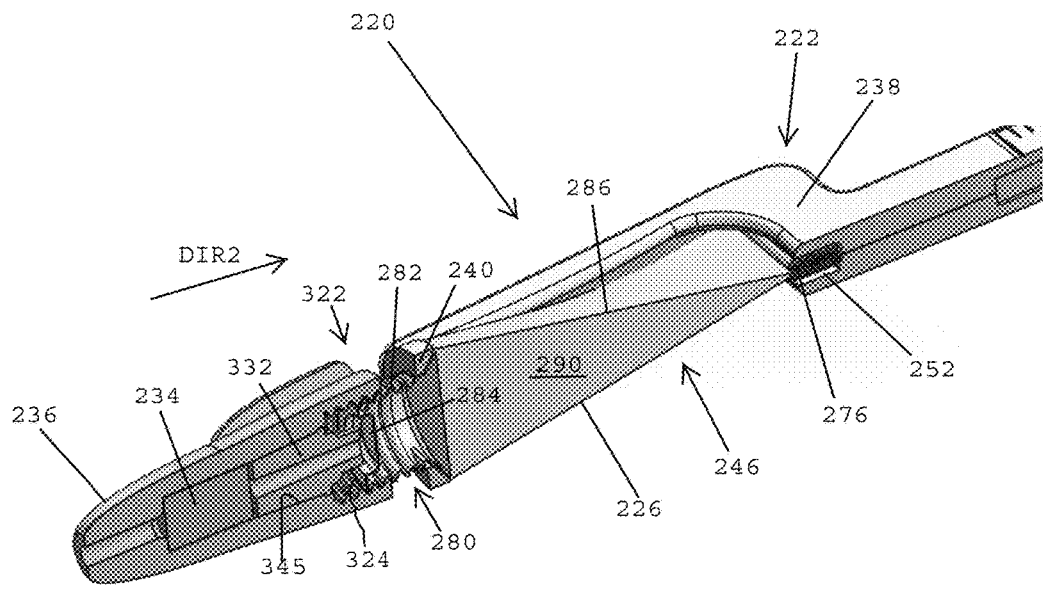
FIG. 16 shows the delivery system of FIGS. 14 and 15 prior to breaking a seal of the squeezable container.

FIG. 16 shows the delivery system 220 with the dispensing cap 236 assembled with the distal end of the squeezable container 226, but prior to breaching the breakable seal 284 of the squeezable container 226. In one embodiment, the female threads 324 at the proximal end 322 of the dispensing cap 236 are threaded onto the external threads 282 of the dispensing neck 280 of the squeezable container 226. In one embodiment, the folded over sealed tail 276 is secured (e.g., wedged) within the proximal trough 252 adjacent the proximal edge 238 of the container support frame 222 for securely affixing the squeezable container to the container support frame 222. The outer wall 286 of the squeezable container 226 is preferably accessible through the central opening 246 of the container support frame 222. The dispensing neck 280 of the squeezable container 226 is preferably secured within the circular opening defined by the distal edge 240 of the container support frame 222. In one embodiment, the distal edge 240 preferably forms a snug fit with the outer surface of the dispensing neck 280 so that the distal end of the squeezable container 226 does not shift and/or move during use of the delivery system 220 disclosed herein.

In one embodiment, the piercer 232 is preferably disposed within the piercer chamber 345 of the dispensing cap 236. The sharpened point 310 (FIG. 12A) at the proximal end of the piercer preferably opposes the breakable seal 284 of the squeezable container 226. The filter 234 containing a chemical initiator for the flowable substance 290 is preferably positioned within the filter channel 332 (FIG. 13B) of the dispensing cap 236.

At the stage shown in FIG. 16, the dispensing cap 236 is partially threaded onto the external threads 282 of the dispensing neck 280 of the squeezable container 226. The breakable seal 284 remains unbroken and the sharpened point 310 at the proximal end of the piercer 332 is distal to the breakable seal 284. Further rotation of the dispensing cap 236 relative to external threads 282 of the dispensing neck 280 will move the dispensing cap 236 in the proximal direction designated DIR2.

Figure 17:
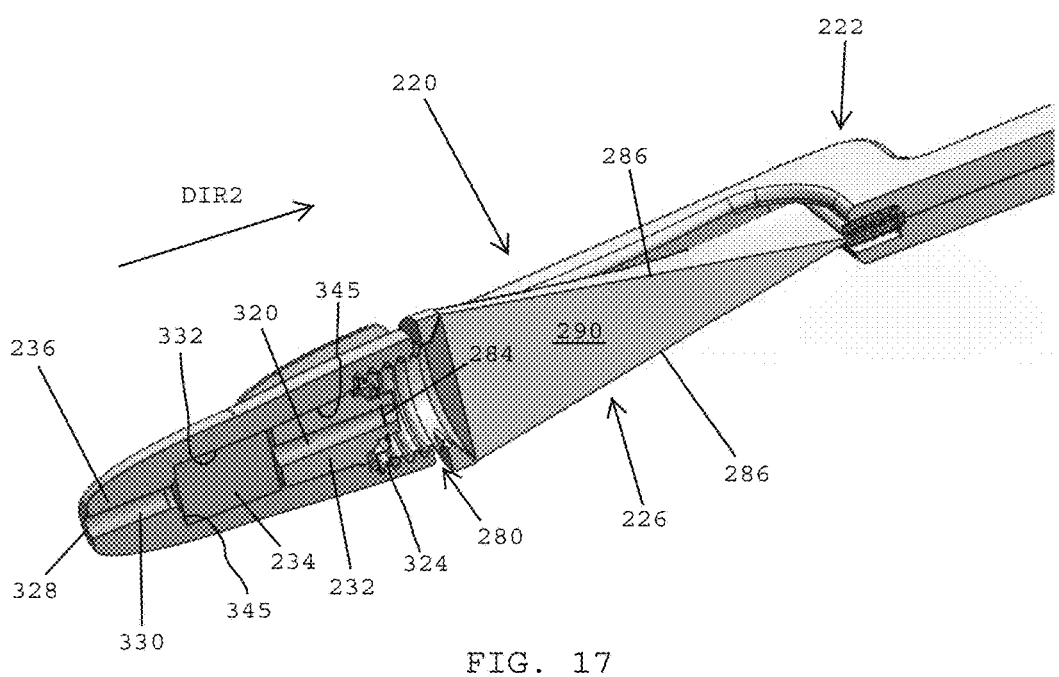
FIG. 17 shows the delivery system of FIGS. 14 and 15 after the seal of the squeezable container has been broken.

FIG. 17 shows the dispensing cap 236 after it has been further rotated relative to the external threads of the dispensing neck of the squeezable container. In one embodiment, as the dispensing cap 236 is rotated, the dispensing cap 236 moves in the proximal direction designated DIR2. The distal end wall 335 of the filter chamber 332 preferably abuts against a distal end of the filter 234 which moves the filter 234 in the proximal direction DIR2. As the filter 234 moves proximally, the filter, in turn, engages a distal end of the piercer 232 for moving the piercer proximally in the direction DIR2 so that the sharpened point 110 (FIG. 12A) of the piercer 232 breaks the seal 284 at the distal end of the squeezable container 226. Proximal movement of the piercer 232 is halted when the dispensing cap 236 is fully threaded onto the external threads of the dispensing neck of the squeezable container.

Once the seal 284 has been broken, the outer walls 286 of the squeezable container 226 may be compressed for forcing the flowable substance 290 stored in the container through the dispensing neck 280, the piercer flow channel 320, the filter 234, and the dispensing cap flow channel 330 for being dispensed from the dispensing aperture 328.

In one embodiment, as the dispensing cap 236 is being rotated for breaking the seal with the piercer, an operator preferably holds the squeezable container 226 via the container support frame 222 so that an operator does not have to engage the side walls 286 of the squeezable container 226 during the unsealing stage, which could prematurely dispense the stored substance as the seal is broken. Thus, in one embodiment, the seal may be broken without physically contacting the squeezable container 226, which minimizes inadvertent and/or accident leakage of the flowable substance 290 from the dispensing neck 280. The structure disclosed herein preferably isolates the step of breaking the seal from the step of squeezing the container to dispense a flowable substance so as to minimize leakage and/or discharge of excessive amounts of flowable substances from a squeezable container.

In one embodiment, the squeezable container is preferably adapted to hold a topical adhesive or sealant material.

In one embodiment, the squeezable container includes a collapsible tube made of metal, plastic or cellulose material. In one embodiment, the breakable seal may include frangible or pierceable metal, foil, plastic, or paper.

In one embodiment, the container support frame is made of two parts that are assembled together. In one embodiment, the two parts have opposing snap-fit projections and depressions that are configured to engage one another for securing the first and second parts together.

In one embodiment, after the squeezable container has been secured within the first and second halves of the container support frame, the top and bottom major surfaces of the squeezable container are desirably are accessible through the central openings so that the sides of the tube may be selectively squeezed for dispensing a flowable substance such as a topical skin adhesive.

In one embodiment, the first and second halves of the container support frame preferably hold the squeezable container via a folded over, sealed tail seal 82 and the distal edge of the support frame engaging the male threaded neck of the squeezable container. The first and second lateral edges of the container support frame preferably cover and protect the sides of the squeezable container so as to minimize accidental squeezing or engagement of the squeezable container.

In one embodiment, the dispensing cap may be rotated about its longitudinal axis for shifting the filter and the piercer in a proximal direction designated for piercing a seal and allowing a flowable substance (e.g., an adhesive) to flow through a piercer channel, the filter, and a dispensing cap flow channel for being dispensed from the dispensing aperture at the distal end of the dispensing cap.

In one embodiment, the elongated handle of the container support frame may be cradled between a surgeon's thumb and index finger for controlling dispensing of the flowable solution from the dispensing cap. Although the present invention is not limited by any particular theory of operation, it is believe that the elongated handle enhances a user's control over the squeezable container and enhances control over where the flowable solution is dispensed.

In one embodiment, the container support frame has two halves that enclose a squeezable container. In one embodiment, the two halves may be assembled together by either press fitting or welding, such as ultrasonic welding, RF welding, or by adhesive bonding. In one embodiment, the squeezable container may be pressed through central openings and/or windows provided on the container support frame to dispense the flowable substance. In one embodiment, the edges of the container support frame provide surfaces that can be engaged when rotating the dispensing cap to break the seal without requiring a user to directly touch the squeezable container so as to avoid directly twisting the relatively weak walls of the squeezable container, thereby preventing accidental tube distortion and premature leaking.

In one embodiment, the proximal end of the elongated handle provides a curved or blade-like surface to provide a readily available structure for smoothing out the dispensed flowable substance (e.g., an adhesive) to provide for uniform substance application. In one embodiment, the elongated handle has a scale or markings such as the markings found on a ruler for measuring distances, such as the length of a wound.

In one embodiment, the piercer has a cutting edge or a sharpened point for breaking the seal at the distal end of a squeezable container. In one embodiment, the piercer has an internal flow channel for directing the flow of the flowable substance through the piercer. In one embodiment, the piercer has a main body with an outer surface having a luer design to prevent leaking of the flowable substance.

In one embodiment, the squeezable container is preferably a tube that may be made of aluminum, plastic, polymers, cellulose, or other collapsible materials. In one embodiment, the squeezable container tube has a breakable seal (e.g., a foil seal) located at a distal end thereof.

In one embodiment, a delivery system for adhesive includes a connector that is permanently attached to the distal end of an adhesive tube to prevent leaking from the flight. In one embodiment, a piercer and a filter are contained inside the connector. In one embodiment, the connector includes a quick turn, luer connection whereby only a half of a turn of a dispensing cap is required to activate the device.

In one embodiment, a delivery system for topical adhesive prevents accidental leaking of the adhesive and distortion of the tube container, thereby providing controllable adhesive application, insuring a good steady grip, providing ease of use and accuracy of delivery, and therefore, improving cosmetic appearance on the healed wound site.

In one embodiment, the container support frame provides protection of the squeezable container (e.g., an adhesive tube) from accidental squeezing and twisting during activation of the flowable substance. The container support frame desirably provides a way for holding the squeezable container for activating the delivery system for use without squeezing or twisting the side walls of the container. The delivery system also enables the device to be activated by twisting the dispensing cap and the container support frame without touching the squeezable container.

In one embodiment, the elongated handle of the container support frame provides an extension that enables a user to enjoy enhanced control and more stable application of the flowable substance.

While the foregoing is directed to embodiments of the present invention, other and further embodiments of the invention may be devised without departing from the basic scope thereof, which is only limited by the scope of the claims that follow. For example, the present invention contemplates that any of the features shown in any of the embodiments described herein, or incorporated by reference herein, may be incorporated with any of the features shown in any of the other embodiments described herein, or incorporated by reference herein, and still fall within the scope of the present invention.

What is claimed is:

1. A delivery system for flowable substances comprising:
   a squeezable container including a sealed proximal end, a distal end having a dispensing neck, and an outer wall extending between said sealed proximal end and said distal end that surrounds a storage reservoir of said squeezable container;
   a container support frame assembled with said squeezable container, said container support frame having a proximal edge that is secured to said sealed proximal end of said squeezable container, a distal edge that is secured to said dispensing neck of said squeezable container, and first and second lateral edges extending between said proximal and distal edges and overlying opposing sides of said squeezable container, wherein said proximal and distal edges and said first and second lateral edges define a central opening of said container support frame that provides access to said outer wall of said squeezable container;
   said container support frame further comprising an elongated handle that extends proximally from said proximal edge of said container support frame, wherein said elongated handle comprises an elongated blade having a proximal end with a rounded surface, wherein said elongated blade has flat top and bottom surfaces that extend between said proximal edge and said rounded surface, and wherein said flat top surface includes markings for measuring distances.

2. The delivery system as claimed in claim 1, wherein said squeezable container comprises a compressible tube made of materials selected from the group consisting of metals, plastics, and cellulose, and wherein said storage reservoir contains a liquid polymerizable adhesive.

3. The delivery system as claimed in claim 1, wherein said squeezable container further comprises:
   external threads provided on said dispensing neck;
   a breakable seal located between a distal end of said dispensing neck and a distal end of said storage reservoir.

4. The delivery system as claimed in claim 3, further comprising:
   a connector having a proximal end with female threads that are threaded onto said external threads of said dispensing neck, said connector including a distal end with a male luer fitting having external threads and a connector flow channel located inside said male luer fitting;
   a dispensing cap having a proximal end including a female luer fitting that matches said male luer fitting of said connector, said dispensing cap including female threads that mesh with said external threads of said male luer fitting, said dispensing cap including a distal end with a dispensing aperture and a dispensing cap flow channel that extends proximally from said dispensing aperture;
   a piercer disposed inside said dispensing cap and within said connector flow channel of said connector, said piercer having a proximal end with a sharpened surface and being configured to slide inside said connector flow channel, wherein said female threads of said dispensing cap are rotatable about said external threads of said male luer fitting of said connector for moving said dispensing cap proximally, which, in turn, advances said piercer proximally for piercing said breakable seal with said sharpened surface of said piercer.

5. The delivery system as claimed in claim 4, wherein said piercer comprises a piercer flow channel that is in axial alignment with said connector flow channel and said dispensing cap flow channel.

6. The delivery system as claimed in claim 5, wherein said dispensing cap further comprises a ring shaped groove that surrounds said dispensing cap flow channel and that seats a distal end of said male luer fitting of said connector.

7. The delivery system as claimed in claim 4, further comprising:
   a porous filter impregnated with a chemical initiator being disposed within said connector flow channel between a distal end of said piercer and a proximal end of said dispensing cap flow channel, wherein said porous filter is configured to slide inside said connector flow channel.

8. The delivery system as claimed in claim 3, further comprising:
   a dispensing cap having a proximal end with female threads that mesh with said external threads of said dispensing neck of said squeezable container, said dispensing cap including a distal end with a dispensing aperture and a dispensing cap flow channel that extends proximally from said dispensing aperture;

a piercer disposed inside said dispensing cap and proximal to said dispensing cap flow channel, said piercer having a proximal end with a sharpened surface, wherein said dispensing cap is rotatable about said external threads of said dispensing neck of said squeezable container for moving said dispensing cap proximally, which, in turn, advances said piercer proximally for piercing said breakable seal with said sharpened surface of said piercer.

9. The delivery system as claimed in claim 8, further comprising:

a porous filter impregnated with a chemical initiator being disposed inside said dispenser cap between a proximal end of said dispensing cap flow channel and a distal end of said piercer.

10. A delivery system for flowable substances comprising:

a squeezable container including a sealed proximal end, a sealed distal end having a threaded dispensing neck and a breakable seal, and an outer wall extending between said sealed proximal end and said sealed distal end that surrounds a storage reservoir of said squeezable container that holds a flowable substance;

a container support frame assembled with said squeezable container, said container support frame having a proximal edge secured to said sealed proximal end of said squeezable container, a distal edge secured to said threaded dispensing neck of said squeezable container, and first and second lateral edges extending between said proximal and distal edges and overlying opposing sides of said squeezable container, wherein said proximal and distal edges and said first and second lateral edges define a central opening of said container support frame that provides access to said outer wall of said squeezable container, and wherein said container support frame further comprises an elongated handle that extends proximally from said proximal edge of said container support frame;

a dispensing cap having a proximal end coupled with said threaded dispensing neck of said squeezable container, said dispensing cap including a distal end with a dispensing aperture and a dispensing cap flow channel that extends proximally from said dispensing aperture;

a piercer disposed inside said dispensing cap, said piercer having a proximal end with a sharpened surface, wherein said dispensing cap is rotatable relative to said threaded dispensing neck of said squeezable container for moving said dispensing cap proximally, which, in turn, slides said piercer proximally for piercing said breakable seal with said sharpened surface of said piercer; and a porous filter impregnated with a chemical initiator and being disposed inside said dispensing cap between a proximal end of said dispensing cap flow channel and a distal end of said piercer.

11. The delivery system as claimed in claim 10, wherein said piercer comprises a piercer flow channel that extends between said proximal and distal ends of said piercer, wherein said piercer flow channel is in axial alignment with said filter and said dispensing cap flow channel.

12. The delivery system as claimed in claim 11, further comprising:

a connector having a proximal end with female threads that are threaded onto said external threads of said dispensing neck, said connector including a distal end with a male luer fitting having external threads and a connector flow channel located inside said male luer fitting;

said dispensing cap having a proximal end including a female luer fitting that matches said male luer fitting of said connector, said dispensing cap including female threads that mesh with said external threads of said male luer fitting;

said porous filter impregnated with a chemical initiator being disposed within said connector flow channel adjacent a proximal end of said dispensing cap flow channel, wherein said porous filter is configured to slide inside said connector flow channel;

said piercer being disposed within said connector flow channel of said connector and being configured to slide inside said connector flow channel, wherein said dispensing cap is rotatable about said external threads of said male luer fitting of said connector for moving said dispensing cap proximally, which, in turn, slides said porous filter proximally, which, in turn, slides said piercer proximally for piercing said breakable seal with said sharpened surface of said piercer.

13. The delivery system as claimed in claim 10, wherein said elongated handle comprises an elongated blade having a proximal end with a rounded surface, wherein said elongated blade has flat top and bottom surfaces that extend between said proximal edge of said container support frame and said rounded surface of said elongated blade, and wherein said flat top surface of said elongated blade has markings for measuring distances.

14. A delivery system for flowable substances comprising:

a squeezable container including a sealed proximal end, a sealed distal end having a threaded dispensing neck and a breakable seal, and an outer wall extending between said sealed proximal end and said sealed distal end, wherein said outer wall surrounds a storage reservoir containing a flowable substance;

a container support frame assembled with said squeezable container, said container support frame having a proximal edge secured to said sealed proximal end of said squeezable container, a distal edge secured to said dispensing neck of said squeezable container, and first and second lateral edges extending between said proximal and distal edges and overlying opposing sides of said squeezable container, wherein said proximal and distal edges and said first and second lateral edges define a central opening of said container support frame that provides access to said outer wall of said squeezable container, said container support frame further comprising an elongated blade extending proximally from said proximal edge;

a connector having a proximal end with female threads that are threaded onto said external threads of said dispensing neck, said connector including a distal end with a male luer fitting having external threads and a connector flow channel located inside said male luer fitting;

a dispensing cap having a proximal end including a female luer fitting that matches said male luer fitting of said connector, said dispensing cap including female threads that mesh with said external threads of said male luer fitting, said dispensing cap including a distal end with a dispensing aperture and a dispensing cap flow channel that extends proximally from said dispensing aperture;

a porous filter impregnated with a chemical initiator, activator, catalyst, crosslinker or other additives being disposed within said connector flow channel adjacent a proximal end of said dispensing cap flow channel, wherein said porous filter is configured to slide inside said connector flow channel;

a piercer disposed inside said dispensing cap and within said connector flow channel of said connector, said piercer being proximal to said porous filter and having a proximal end with a sharpened surface, wherein said female threads of said dispensing cap are rotatable about said external threads of said male luer fitting of said connector for moving said dispensing cap proximally, which, in turn, slides said porous filter proximally, which, in turn, slides said piercer proximally for piercing said breakable seal with said sharpened surface of said piercer.

15. The delivery system as claimed in claim 14, wherein said elongated blade has a proximal end with a rounded surface, wherein said elongated blade has flat top and bottom surfaces that extend between said proximal edge of said container support frame and said rounded surface of said elongated blade, and wherein said elongated blade has markings provided on said flat top surface for measuring distances.

16. The delivery system as claimed in claim 14, wherein said piercer comprises a piercer flow channel that is in axial alignment with said connector flow channel, said porous filter, said dispensing cap flow channel, and said dispensing aperture, and wherein after said breakable seal has been pierced, said outer wall of said squeezable container is compressible for forcing said flowable substance through said piercer flow channel, said connector flow channel, said filter, said dispensing cap flow channel, and said dispensing aperture.

17. The delivery system as claimed in claim 14, wherein said dispensing cap further comprises a ring shaped groove that surrounds said dispensing cap flow channel and has an open end that faces toward said proximal end of said dispensing cap for seating a distal end of said male luer fitting of said connector.

\* \* \* \* \*